US009381640B2

(12) United States Patent
Van Der Linde et al.

(10) Patent No.: US 9,381,640 B2
(45) Date of Patent: Jul. 5, 2016

(54) POWER TOOL STORAGE AND PACKAGE SYSTEM

(71) Applicant: DEMAIN TECHNOLOGY PTY LTD, Heatherton (AU)

(72) Inventors: Benjamin Luke Van Der Linde, Heatherton (AU); David Leigh Scrimshaw, Heatherton (AU); Paul Francis Connor, Heatherton (AU); Paul Miller, Heatherton (AU); Ben Eyers, Heatherton (AU); Sion Netzler, Heatherton (AU); Lucas Lastman, Heatherton (AU)

(73) Assignee: DEMAIN TECHNOLOGY PTY LTD, Victoria (AU)

( * ) Notice: Subject to any disclaimer, the term of this patent is extended or adjusted under 35 U.S.C. 154(b) by 0 days.

(21) Appl. No.: 14/137,762

(22) Filed: Dec. 20, 2013

(65) Prior Publication Data

US 2014/0312033 A1 Oct. 23, 2014

Related U.S. Application Data

(63) Continuation of application No. 13/594,515, filed on Aug. 24, 2012, now abandoned, which is a continuation of application No. PCT/AU2011/000211, filed on Feb. 25, 2011.

(30) Foreign Application Priority Data

Feb. 25, 2010 (AU) ................................ 2010900807
Feb. 25, 2010 (AU) ................................ 2010900808
Feb. 25, 2010 (AU) ................................ 2010900809
Feb. 26, 2010 (AU) ................................ 2010900831
Nov. 29, 2010 (AU) ................................ 2010905259

(51) Int. Cl.
*B25H 3/02* (2006.01)
*B25H 3/00* (2006.01)

(Continued)

(52) U.S. Cl.
CPC ................ *B25H 3/023* (2013.01); *A47B 88/20* (2013.01); *B25H 3/006* (2013.01); *B65D 25/10* (2013.01); *B65D 25/2835* (2013.01); *A47B 2088/202* (2013.01)

(58) Field of Classification Search
CPC .. A47B 2088/202; A47B 88/20; B25H 3/006; B25H 3/023; B65D 25/2835; B65D 25/10
USPC ............ 220/23.83, 23.86, 23.87, 23.89, 694, 220/735; 206/503, 504
See application file for complete search history.

(56) References Cited

U.S. PATENT DOCUMENTS 3,370,697 A 2/1968 Levey et al.
3,969,796 A 7/1976 Hodsdon et al.

(Continued)

FOREIGN PATENT DOCUMENTS

DE 42 29 420 A1 3/1993
DE 4229420 A1 3/1993

(Continued)

*Primary Examiner* — Robert J Hicks
*Assistant Examiner* — Kareen Thomas
(74) *Attorney, Agent, or Firm* — Sughrue Mion, PLLC

(57) ABSTRACT

A storage system for a power component comprising a receptacle including a base and a closure connected to the base, the base and the closure defining an internal space for receiving one or more components, the closure being operable for selectively enclosing the internal space, and a connection means for releasably connecting the base with at least one component that is positioned within the internal space of the receptacle, the connection means including a first connection portion associated with the base for connecting with a second connection portion of the component. A package for containing a product interfacing device with a surface defining a recess that is shaped to conform with an exterior surface of the product and thereby restrict movement of the product relative to the product interfacing device, a removable cover and a connection means for releasably connecting the product interfacing device within the internal space of a receptacle.

18 Claims, 19 Drawing Sheets

(51) Int. Cl.

| | |
|---|---|
| ***A47B 88/20*** | (2006.01) |
| ***B65D 25/10*** | (2006.01) |
| ***B65D 25/28*** | (2006.01) |

(56) References Cited

U.S. PATENT DOCUMENTS

| | | | | |
|---|---|---|---|---|
| 3,983,977 | A | 10/1976 | Crabb | |
| 3,986,765 | A | 10/1976 | Shaffer et al. | |
| 4,083,621 | A | 4/1978 | Davidson et al. | |
| 4,619,363 | A * | 10/1986 | Wolfseder | B65D 21/0224 206/372 |
| 4,685,634 | A | 8/1987 | Schwartz | |
| 5,083,241 | A | 1/1992 | Foster | |
| 5,084,598 | A | 1/1992 | Nagata et al. | |
| 5,356,004 | A | 10/1994 | Weinreb | |
| 5,418,701 | A | 5/1995 | Hart | |
| 5,509,704 | A | 4/1996 | Schneider et al. | |
| 5,657,841 | A | 8/1997 | Morvan | |
| 5,984,441 | A | 11/1999 | Stokhuijzen | |
| 6,099,812 | A * | 8/2000 | Allen | A61L 2/26 206/370 |
| 6,181,032 | B1 | 1/2001 | Marshall et al. | |
| 6,206,107 | B1 | 3/2001 | Wadge | |
| 6,206,493 | B1 | 3/2001 | Sanchez-Levin et al. | |
| 6,286,611 | B1 | 9/2001 | Bone | |
| 6,368,133 | B1 | 4/2002 | Zeiler et al. | |
| 6,443,675 | B1 | 9/2002 | Kopras et al. | |
| 6,609,924 | B2 | 8/2003 | Zeiler et al. | |
| 6,729,415 | B1 | 5/2004 | Huang | |
| 6,796,389 | B2 | 9/2004 | Pusateri et al. | |
| 7,184,259 | B2 | 2/2007 | Marler et al. | |
| 7,246,704 | B2 * | 7/2007 | Brunson | B25H 3/023 206/372 |
| 7,341,148 | B2 * | 3/2008 | Bettenhausen | A61B 19/026 206/370 |
| 7,414,211 | B2 | 8/2008 | Elsworthy | |
| 2003/0070822 | A1 | 4/2003 | Kanzaki et al. | |
| 2003/0089603 | A1 * | 5/2003 | Scheer et al. | 204/424 |
| 2005/0031458 | A1 * | 2/2005 | Brashears | 417/234 |
| 2005/0045510 | A1 | 3/2005 | Marks | |
| 2005/0218867 | A1 | 10/2005 | Phillips et al. | |
| 2006/0037766 | A1 | 2/2006 | Gass et al. | |
| 2008/0041207 | A1 | 2/2008 | Chen | |
| 2008/0237939 | A1 | 10/2008 | McDonnough et al. | |
| 2009/0174998 | A1 | 7/2009 | Struthers et al. | |
| 2010/0224527 | A1 | 9/2010 | Huang | |
| 2011/0168729 | A1 * | 7/2011 | Koenig | B65D 25/2858 220/761 |
| 2012/0104991 | A1 * | 5/2012 | Suzuki | H01M 2/1055 320/103 |

FOREIGN PATENT DOCUMENTS

| | | | |
|---|---|---|---|
| DE | 298 07 975 | U1 | 7/1998 |
| DE | 20 2009 007 077 | U1 | 7/2009 |
| DE | 20 2009 007 599 | U1 | 9/2009 |
| DE | 20 2009 012 602 | U1 | 3/2011 |
| EP | 1 863 107 | A1 | 4/2007 |
| ES | 1674217 | A1 | 6/2006 |
| WO | 2006/046967 | A1 | 5/2006 |

* cited by examiner

FIG 3
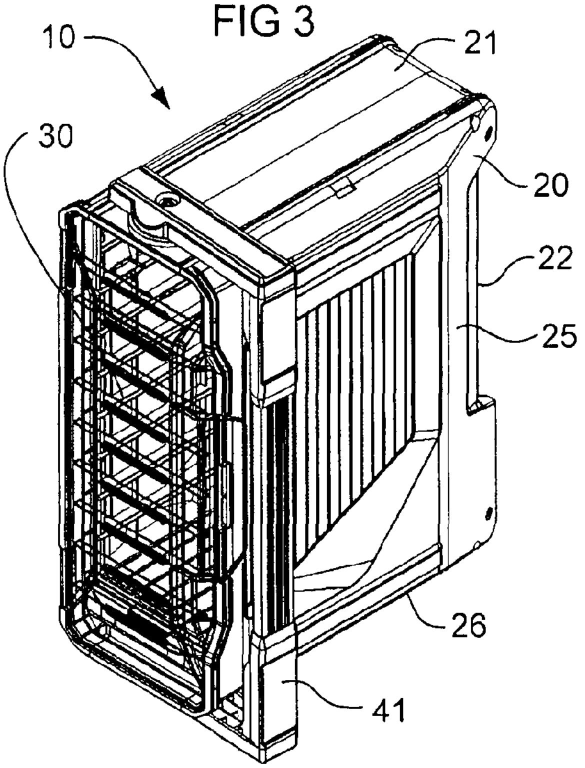
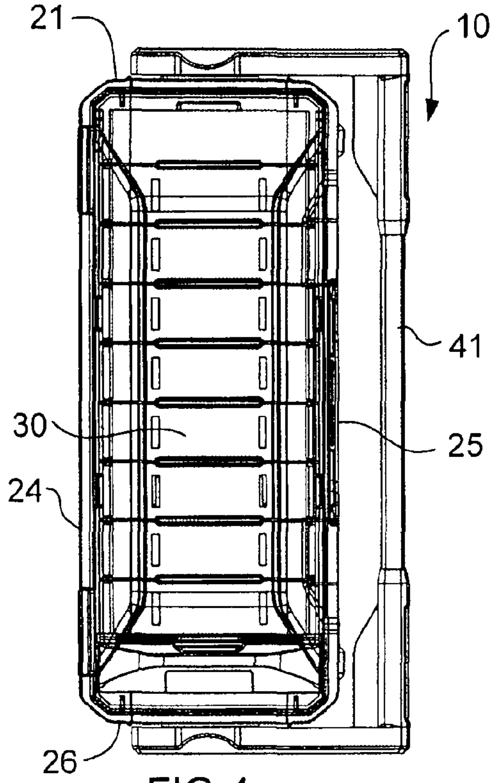
FIG 4
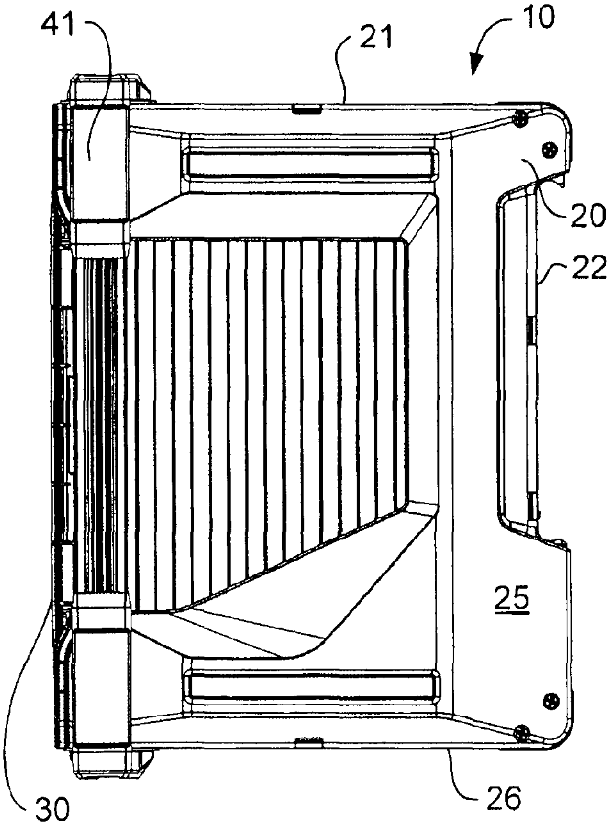
FIG 5
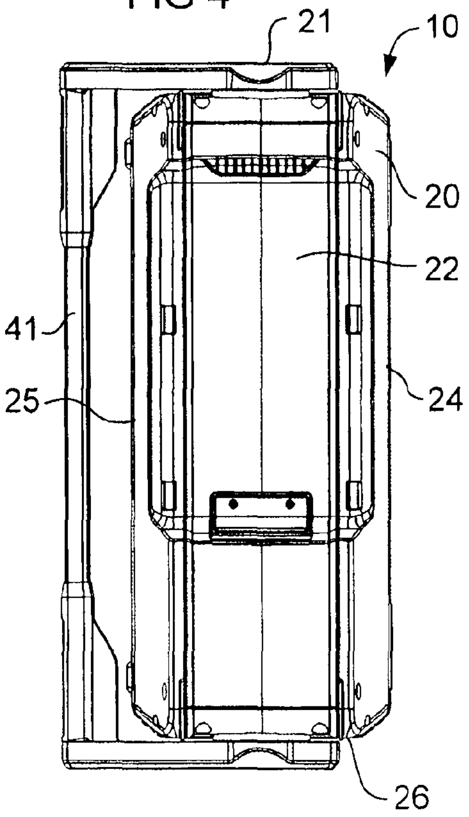
FIG 6

POWER TOOL STORAGE AND PACKAGE SYSTEM

CROSS REFERENCE TO RELATED APPLICATIONS

This application is a Continuation of U.S. application Ser. No. 13/594,515, filed Aug. 24, 2012, which is a is a §371 National Stage Application of International Application No. PCT/AU2011/000211 filed on Feb. 25, 2011, which claims priority from Australian Patent Application Nos. 2010900808, AU 2010900831, AU 2010900809, AU 2010900807, filed on Feb. 25, 2010, and AU 20109090529, filed Nov. 29, 2010, the contents of all of which are incorporated herein by reference in their entirety.

FIELD OF THE INVENTION

The present invention relates to the field of power tool storage devices and power tool packaging.

BACKGROUND OF THE INVENTION

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

Power tools are typically marketed and sold in hardware stores and retail outlets in some form of packaging. Power tools can be packaged in a variety of forms including providing the power tool in a disposable cardboard container, a disposable polymer container, such as a blister pack, or in a durable plastic or metal container or case intended for containing and storing the power tool throughout its usable life.

An advantage of packaging and marketing power tools in a disposable container, such as a cardboard or disposal plastic container, is that such packaging is relatively inexpensive when compared with durable packaging arrangements such as power tool containers or cases made out of substantially rigid plastic or metal. Accordingly, power tools packaged in disposable packaging can be offered to consumers at a relatively cheaper price compared with power tools packaged in durable containers or cases. When a user is presented with a selection of power tools for purchase they may be attracted towards purchasing a power tool packaged in disposable packaging offered at a cheaper price than an equivalent power tool packaged in a durable storage container or case. However, the same consumer may, at a later date, wish to be able to store the purchased power tool in a durable container or case but may not be able to purchase such a container or case as durable power tool storage containers or cases are typically only marketed for sale along with a new power tool. Otherwise, durable storage containers or cases that may be available for sale separately will not be designed to contain and store a particular power tool.

Existing packages for storing power tools, such as power tool cases, are used to contain the power tool from the moment of manufacture, through to transport of the power tool to display on a retail shelf for sale to a consumer. As such, existing power tool storage cases are designed to contain a predetermined array of contents including the power tool and associated essentials such as a battery, a charger and in some cases a small array of accessories to be used with the power tool such that the overall size of the package is as small as possible to save space during transportation, storage and on retail shelves. Furthermore, existing packages for power tools do not allow for relatively neat and tidy storage.

Accordingly, it would be advantageous to be able to provide a power tool packaging arrangement that is relatively inexpensive, so that the price at which the power tool is offered for sale can be as low a possible, yet also provide consumers with the option of separately purchasing a durable power tool storage receptacle, such as a container or case, that is capable of securely receiving a separately purchased power tool. It would also be advantageous to be able to provide a consumer with the option of purchasing a durable power tool storage receptacle that is effectively designed to securely receive a power tool yet does not necessitate marketing a variety of different power tool storage cases each specifically designed for a specific power tool.

It would be advantageous to be able to provide a storage system for a product that can be stored and transported in such a manner as to save space during storage and transportation and on retail shelves yet can also contain a broader array of contents beyond a predetermined array of contents such as a power tool and associated essentials such as a battery, a charger and in some cases a small array of accessories. It would also be advantageous to provide a receptacle that is capable of containing and holding a power tool, or other device, and/or accessories that is portable yet provides a neat and tidy storage solution when not required

SUMMARY OF THE INVENTION

Accordingly, in a first aspect, the present invention provides a storage system for a component, including:

- a receptacle including a base and a closure connected to the base, the base and the closure defining an internal space for receiving one or more components, the closure being operable for selectively enclosing the internal space
- a connection means for releasably connecting the base with at least one component that is positioned within the internal space of the receptacle, the connection means including a first connection portion associated with the base for connecting with a second connection portion of the component.

In an embodiment, the base is comprised of one or more wall members and a closure, the wall members and the closure are connected to each other to define an internal space for receiving the component wherein the closure is operable for selectively enclosing the internal space.

In a further embodiment, the base is comprised of at least two wall members that define the internal space and that are configured to be nested within each other in a disassembled condition.

The above forms of the invention are advantageous in that they provides a storage system for a component, which may be a product such as a power tool and/or accessories, wherein the storage system has a knock-down form and can be flat-packed during storage and transportation to save space during storage and transportation. The fact that the storage system has a disassembled form so that it can be flat-packed means that less space is required for the product on retail shelves yet when the storage system is assembled the storage system is sufficiently large to contain a product such as a power tool and additional accessories, tools, fasteners and the like.

In yet another embodiment, the connection means includes spaced apart pairs of the first connection portions, each of the pairs of first connecting portions for connecting with a pair of the second connecting portions of the component.

In a preferred embodiment, the first and second connection portions include a ridge and a groove, wherein the groove is configured to slidably receive the ridge to maintain the component relative to the receptacle.

In still yet another embodiment, each of the pairs of first connecting portions are comprised of a pair of spaced apart openings for receiving the pair of the second connecting portions comprised of a pair of spaced apart cantilever beam snap-fitting members.

In one embodiment, the component is a product interfacing device that includes an interface surface defining a recess that is shaped to conform with an exterior surface of the product and thereby restrict movement of the product relative to the product interfacing device.

In another embodiment, the product interfacing device includes first and second folding members that are interconnected so as to be foldable relative to each other between a lay-flat condition and an assembled condition, wherein in the assembled condition the first and second folding members are positioned relative to each other so as to form the interface surface.

In yet another embodiment, in the assembled condition the first and second folding members are positioned relative to each other so as to form the second connection portion of the product interfacing device.

In one embodiment, the interface surface is shaped to receive the product within the recess in an interference fit.

In another embodiment, the product interfacing device includes opposing tabs for receiving and squeezing the product therebetween when the product is received within the recess.

In yet another embodiment, the component includes one or more drawers each including a recess for receiving a product, wherein each one of the drawers is movable relative to the base between a closed position for enclosing the product within the recess and an open position for enabling access to the product within the recess.

In still yet another embodiment, the first and second connection portions include a ridge and a groove, wherein the groove is configured to slidably receive the ridge to retain the drawer within the internal space of the receptacle.

In a preferred form, the product interfacing device forms part of a package for containing the product independently of the receptacle. Preferably, the interfacing device is formed from injection or blow moulded polymer.

In one embodiment, the product is any one of a group including a power tool, an electrical device, an electronic device, a hand held power tool, a hand held electrical device and a hand held electronic device and combinations thereof.

In a second aspect, the present invention provides a package for containing a product including:

a product interfacing device including an interface surface defining a recess that is shaped to conform with an exterior surface of the product and thereby restrict movement of the product relative to the product interfacing device, a removable cover coupled to the interfacing device for enclosing the product when the cover is coupled to the interfacing device and for enabling access to the product when removed from the interface member, wherein the product interfacing device includes a connection means for releasably connecting the product interfacing device within the internal space of a receptacle.

In a preferred embodiment, the connection means includes a first connection portion associated with the product interfacing device for connecting with a second connection portion located within the internal space of the receptacle.

In a further preferred embodiment, the first and second connection portions include a ridge and a groove, wherein the groove is configured to slidably receive the ridge to maintain the product interfacing device relative to the receptacle.

In an embodiment, the product interfacing device includes first and second folding members that are interconnected so as to be foldable relative to each other between a lay-flat condition and an assembled condition, wherein in the assembled condition the first and second folding members are positioned relative to each other so as to form the interface surface.

In another embodiment, in the assembled condition the first and second folding members are positioned relative to each other so as to form a connection portion for connecting the product interfacing device to a receptacle.

In yet another embodiment, the interface surface is shaped to receive the product within the recess in an interference fit.

In still yet another embodiment, the interface member includes opposing tabs for receiving and squeezing the product therebetween when the product is received within the recess.

In one embodiment, the cover includes a viewing portion for viewing the product covered within the recess.

In another embodiment, wherein the cover is formed out of a transparent polymer.

In yet another embodiment, wherein the cover includes a thermoformed polymer.

In still yet another embodiment, the product is any one of a group including a power tool, an electrical device, an electronic device, a hand held power tool, a hand held electrical device and a hand held electronic device.

In an embodiment, the product interfacing device includes pivoting handle member for carrying the product interfacing device.

In a third aspect, the present invention provides a storage receptacle for a product, including:

a base comprised of a pair of wall members and a closure, the wall members and the closure are connected to each other in an assembled condition to define an internal space for receiving a product wherein the closure is operable for selectively enclosing the internal space, a connection means for releasably connecting the base with at least one component that is positioned within the internal space of the receptacle, the connection means including a first connection portion associated with the base for connecting with a second connection portion of the component.

In one embodiment, the wall members are configured to be nested within each other in a disassembled condition.

In another embodiment, the wall members are connected together in a clam-shell arrangement in the assembled condition.

In yet another embodiment, the connection means includes a row of spaced apart pairs of the first connection portions, each of the pairs of first connecting portions for connecting with a pair of the second connecting portions of the component.

In still yet another embodiment, each of the pairs of first connecting portions are comprised of a pair of spaced apart openings for receiving the pair of the second connecting portions comprised of a pair of spaced apart cantilever beam snap-fitting members.

In an embodiment, the first and second connection portions include a ridge and a groove, wherein the groove is configured to slidably receive the ridge to maintain the component relative to the receptacle.

In another embodiment, the component is a product interfacing device that includes an interface surface defining a recess that is shaped to conform to an exterior surface of the product and thereby restrict movement of the product relative to the product interfacing device.

BRIEF DESCRIPTION OF THE DRAWINGS

The present invention will now be described in more detail with reference to the following figures. The following figures represent embodiments of the invention in the form of a storage system for handheld power tools and a package for containing a power tool and for the sake of convenience the present invention will now be described below in detail with reference to this embodiment. It is to be appreciated, however, that the present invention may be suitable for use with a variety of tools such as handheld power tools in the form of handheld power drills, handheld power saws, handheld power screwdrivers, handheld percussion/hammer drills, handheld angle grinders, handheld circular saws, handheld power sanders or other handheld electrical devices such as a light emitting device to name but a few.

FIGS. 3 to 6 illustrate a perspective view, a front view, a side view and a rear view of the power tool receptacle of FIG. 1.

DETAILED DESCRIPTION

Figure 1:
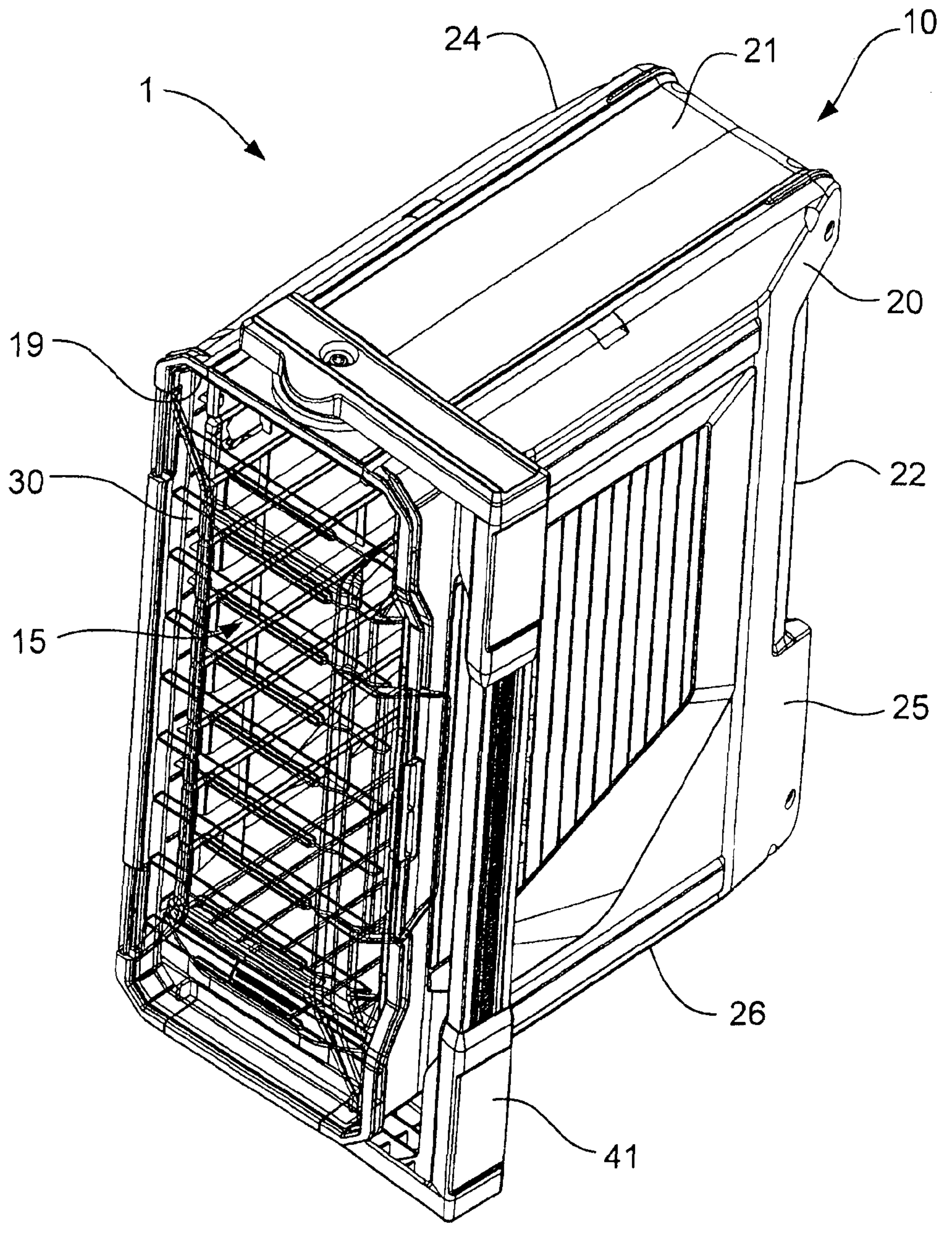
FIG. 1 illustrates a perspective view of a power tool receptacle of a power tool storage system of an embodiment of the invention.

Referring to FIGS. 1 to 14 and 22 to 28 there is shown embodiments of a power tool storage system 1 of the invention. The storage system 1 broadly includes a device receptacle 10 that is configured for receiving a device such as a power tool therewithin. In the illustrated embodiment, the device receptacle 10 is configured for receiving a power tool interfacing device 40, 140, 240, 340 and a handheld power tool, such as a handheld power drill, there within. The receptacle 10 includes a base 20 and a closure member 30. The base 20 and the closure 30 are shaped to provide a generally box shaped member having a substantially hollow internal space 15 that is adapted for receiving the power tool interfacing device 40, 140, 240, 340 and the handheld power tool there within. A handle member 41 in the form of an elongated bar is pivotally attached to the base member 20.

The base 20 includes a base wall member 22, pair of opposite side wall members 23, 25, a pair of opposite end wall members 24, 26. The base wall member 22. the opposite end wall members 24, 26 are positioned between the side wall members 23, 25 when the base 20 is in the assembled condition as illustrated in FIGS. 1 and 3 to 6. The base wall member 22 and the opposite end wall members 24, 26 can be releasably connected to each other and to the side wall members 23, 25 by any means such as by screw fasteners or snap-fitting fasteners. Accordingly, the components of the base 20 may be transported and stored in a knock-down or disassembled form to thereby reduce the amount of space required for storing the base 20. After the components of the receptacle 10, including the base 20 and the closure 30 are purchased by a consumer the components are assembled together as illustrated in FIGS. 1 and 3 to 6.

Referring to FIGS. 1 and 3 to 6, in the assembled condition of the base 20 the pair of opposite end walls 24, 26 are upstanding from the base wall 22 and extend between the side walls 23, 25. A handle member 41 is pivotally attached to the end walls 24, 26 of the base member 20. The base wall 22, the side walls 23, 25 and the end walls 24, 26 of the base member 20 define at least part of the internal space 15. The base 20 may be formed out of any suitable material such as a rigid polymer or metallic material. The opposite end walls 24, 26 and the side walls 23, 25 define an opening 19 to the internal space 15 of the base 20. The opening 19 is located opposite to the base wall 22.

Figure 20:
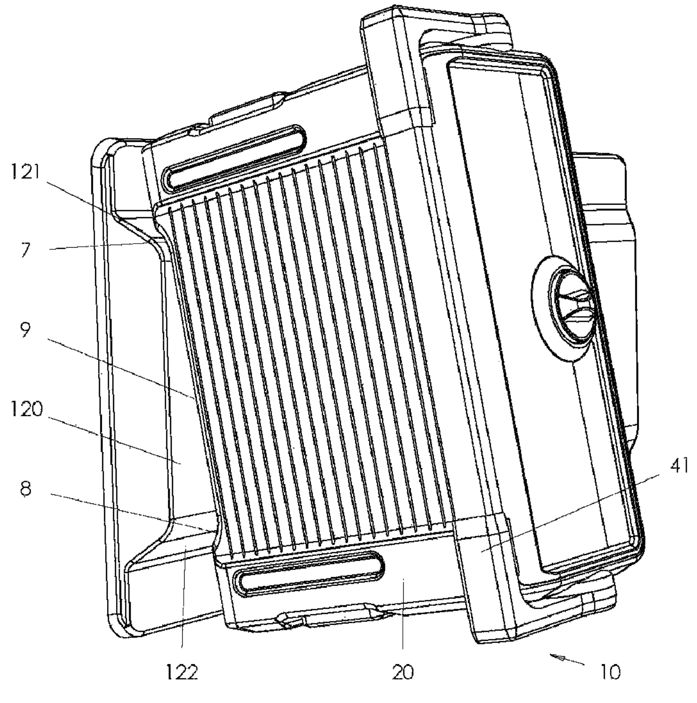
FIG. 20 illustrates a perspective view of the power tool receptacle of FIG. 17 being mounted to a support attached to an upright surface such as a wall.

As can be seen in FIG. 5, the base 20 includes a connecting portion 28 in the form of one or more flanges 7, 8 upstanding and projecting from the base wall 22 of the base 20. The flanges 7, 8 are generally L-shaped or hook shaped members that are spaced apart from each other by a substantially planar facing surface 9. The connecting portion 28 is adapted to connect to a suitably configured support, such as the support 120 illustrated in FIG. 20, mounted to a wall or some other upright surface. In particular, an upper one of the flanges 7 is adapted to rest upon an upper ledge 121 of the support 120 such that the weight of the receptacle 10 is transferred through the upper flange 7 to the upper ledge 121 of the support 120. The lower one of the flanges 8 is adapted to snap fit with a lower ledge 122 of the support 120 in order to retain the connecting portion 28 to the support 120 and, in turn, retain the receptacle 10 to the support 120. When a user wishes to remove the receptacle 10 from the support 120 the user manipulates the receptacle 10 so as to release the lower flange 8 from the lower ledge 122 of the support 120 and then may lift the receptacle 10 to remove the upper flange 7 from the upper ledge 121 of the support 120. The user may then carry the receptacle 10 using the handle member 41 to a desired location. The above described embodiment of the receptacle 10 is advantageous in that it provides a receptacle that is capable of containing and holding a power tool, or other device, and/or accessories that on the one hand is portable and on the other hand can form a cabinet when the receptacle 10 is mounted to the support on an upright surface.

The closure member 30 is adapted to be releasably connected to the base 20 to selectively close the opening 19 to selectively allow or prevent access to the internal space 15 within the base 20. The closure member 30 includes a substantially planar front wall member 32, a pair of opposite side edges 33, 35 and pair of opposite end edges 34, 36 extending between the side edges 33, 35. The closure member 30 is pivotally connected to the base member 20 by at least one and preferably two hinge connections 31 or any other suitable means enabling the closure member 30 to pivot relative to the base member 20 between an open position and a closed position. When the closure member 30 is in the open position the internal space 15 defined within the base portion 20 can be accessed through the opening 19. When the closure member 30 is in the closed position the front wall 32, opposite end walls 34, 36 and opposite side walls 33, 35 define the internal space 15 of the tool receptacle 10. Also, when the closure member 30 is in the closed position the opening 19 is closed and the internal space 15 within the tool receptacle 10 is enclosed thereby preventing access to the internal space 15.

Referring to FIGS. 7 to 16 there are shown two embodiments of the power tool interfacing device 40, 140 that are configured to receive a power tool (not shown) in a manner so as to locate the power tool at a substantially fixed position relative to the interfacing device 40 and, optionally, to retain the power tool. Accordingly, the interfacing device 40 may take any suitable form adapted for this purpose. In the embodiment illustrated in FIGS. 7 to 12, the interfacing device 40 includes a chassis 50 and power tool interface surface 60. The interface surface 60 defines a recess 65 that is shaped to receive the power tool. The chassis 50 includes a base 54 and a frame 58 connected to, and extending from, the base 54. The base 54 and the frame 58 may be formed out of any suitable material such as a rigid or semi rigid polymer or metallic material having a rigidity and/or strength sufficient for the purpose of supporting a power tool. Thus, the interfacing device 40 may be formed out of a durable polymer or metallic material. The frame 58 surrounds and is formed integrally with the interface surface 60. The interface surface 60 is generally in the form of a surface that is recessed within the frame 58 to form a recess 65 or cavity having a shape that corresponds to, or conforms with, the shape of the external surface of the power tool or a least a portion of the external surface of the power tool to be positioned there within. For example, in the embodiment illustrated in the Figures, the interface surface 60 is shaped to conform to the external surface of a handheld power drill-type power tool. Accordingly, the interface surface 60 illustrated in the Figures includes a power drill body housing region 62 shaped to receive the body housing of the power tool and a driven member region 66 shaped to receive the driven member or chuck portion of the power tool. As will be appreciated, the interface surface 60 can be designed for any one of a variety of power tools of types other than hand held power drills and, as such, may have any one or more of these regions or may have other regions entirely that are adapted to conform with the external surface of the particular power tool to be received within the recess 65 defined by the interface surface 60. The interface surface 60 meets the frame 58 along a peripheral edge 61 extending around the periphery of the interface surface 60 and defining an opening 63 through which the power tool is received to the recess 65.

The interface surface 60 may be shaped and/or sized so as to receive the power tool in an interference fit there within. In the embodiment illustrated in FIGS. 7 to 12, the interface surface 60 includes a pair of opposing tabs or fingers 67, 68, that are adapted to receive and squeeze the power tool therebetween when the power tool is received within the recess 65 so as to prevent, limit or restrict movement of the power tool relative to the recess 65 and to prevent, restrict or limit removal of the power tool from within the recess 65.

Although in the embodiments illustrated in FIGS. 7 to 12, the power tool interfacing device 40 is configured to include an interface surface 60 defining a recess 65 for receiving a handheld power drill type of power tool it is to be appreciated that the power tool interfacing device 40 may take any one of a variety of different forms for receiving any one of a variety of power tools. For example, the power tool interfacing device 140 illustrated in FIGS. 13 to 16 is configured to include an interface surface 160 defining a recess 165 for receiving handheld jigsaw power tool (not shown) any one of a variety of handheld power drills, handheld power saws, handheld power screwdrivers, handheld percussion/hammer drills, handheld angle grinders, handheld circular saws, handheld power sanders and other handheld electrical devices such as a light emitting device, such as a torch, a radio or any other hand held and/or portable electrical or electronic device to name but a few. As will be appreciated, the receptacle 10 of embodiments of the invention is capable of receiving and releasably being connected to any one of a variety of interfacing devices 40 for receiving any one of a variety of devices, such as power tools, therewithin in a manner in which the devices are held securely within, and relative to, the receptacle 10.

Figure 23:
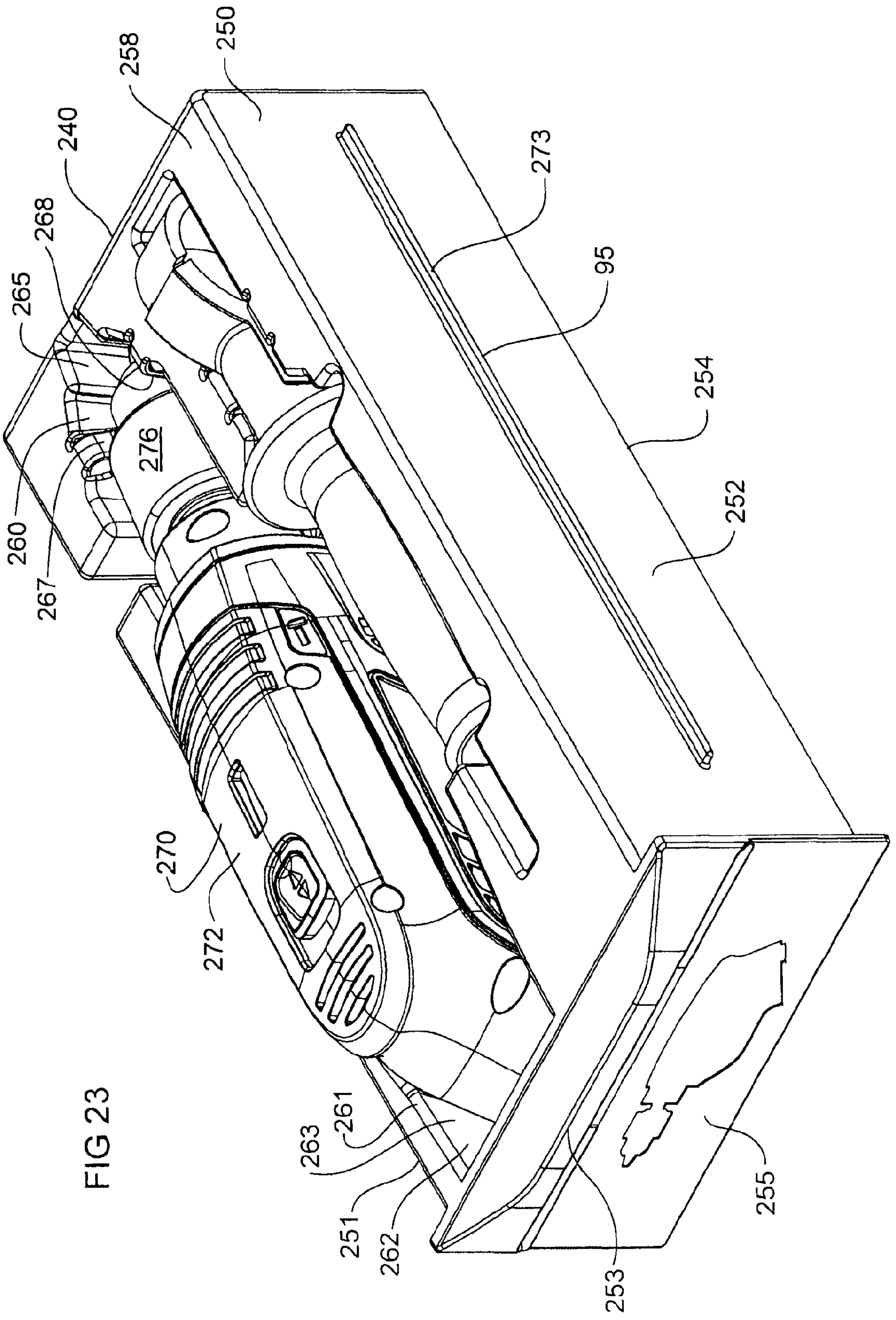
FIG. 23 illustrates a perspective view of a power tool interfacing device of an embodiment of the storage system of the invention wherein the interfacing device contains a hand held power drill module capable of attachment to a power control module and a handle attachment capable of attachment to a forward portion of the drill module.
Figure 24:
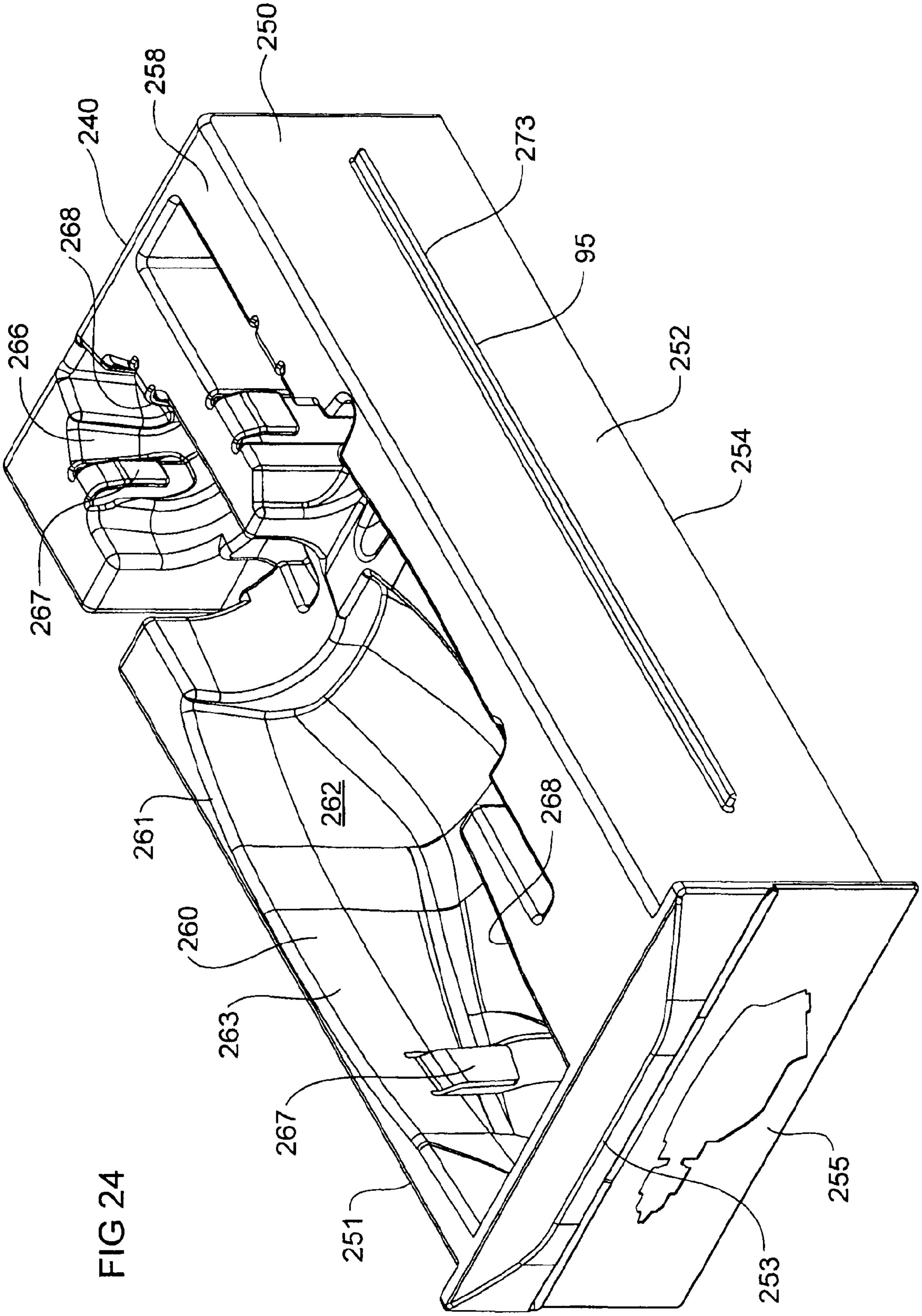
FIG. 24 illustrates a perspective view of the power tool interfacing device of FIG. 23 with the power drill module and the handle attachment removed.
Figure 25:
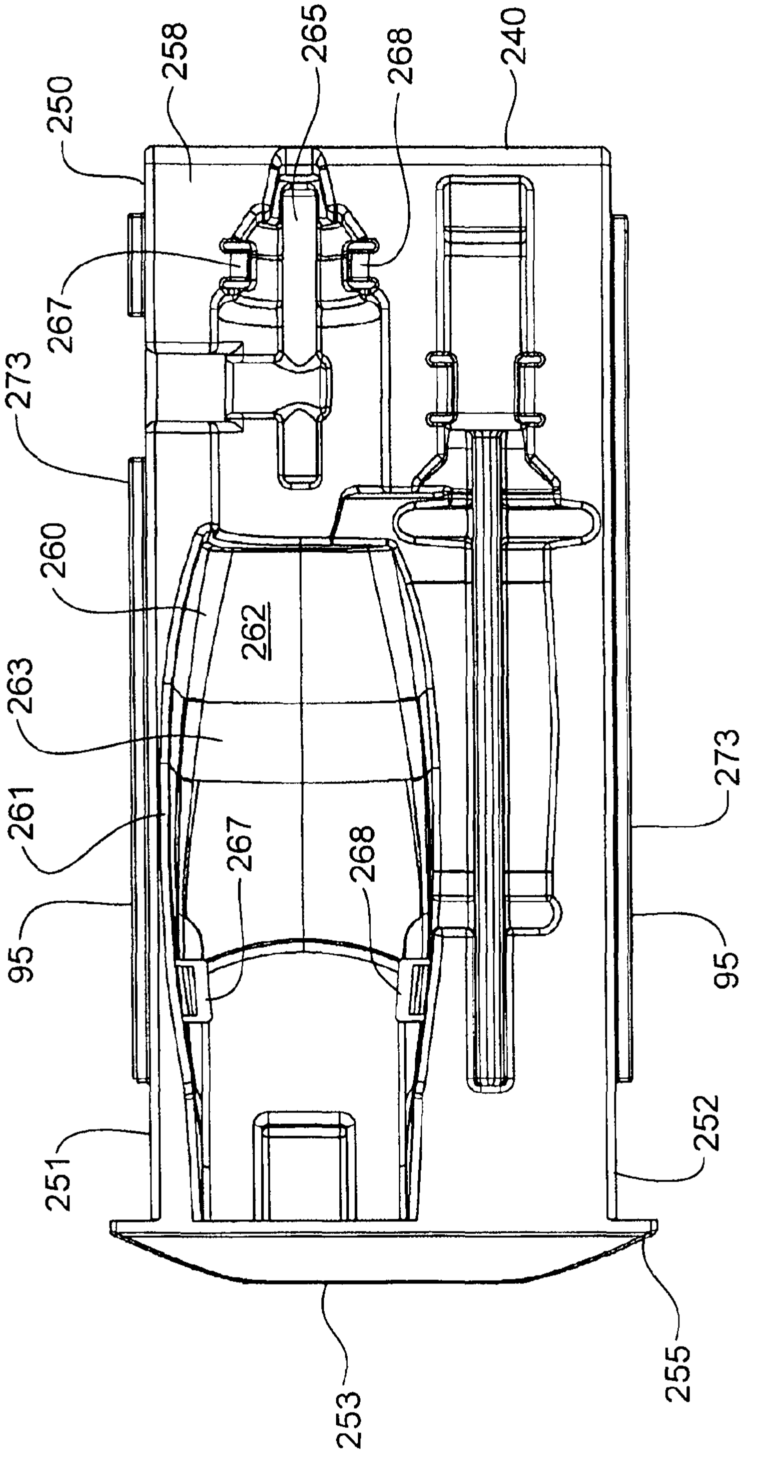
FIG. 25 illustrates a plan view of the power tool interfacing device of FIG. 23 with the power drill module and the handle attachment removed.

Referring to FIGS. 23 to 28 there are shown two embodiments of the product interfacing device 240, 340 that are respectively configured to receive a power tool module 270 and a power control module 370 in a manner so as to locate the power tool 270 and the power control module 370 at a substantially fixed position relative to the interfacing devices 240, 340 and, optionally, to retain the power tool module 270 and the power control module 370. In the embodiment illustrated in FIGS. 23 to 28, the interfacing devices 240, 340 include a chassis 250, 350 and device interface surface 260, 360. Referring to FIGS. 23 to 25 the chassis 250 includes an opposite pair of parallel side walls 251, 252 each including an elongated flange or ridge 273. The interface surfaces 260, 360 each define a recess 265, 365 that is shaped to receive the power tool 270 and the power control module 370 respectively. The chassis 250, 350 includes a base 254, 354 and a frame 258, 358 connected to, and extending from, the base 254, 354. The base 254, 354 and the frame 258, 358 may be formed out of any suitable material such as a rigid or semi rigid polymer or metallic material having a rigidity and/or strength sufficient for the purpose of supporting a power tool. Thus, the interfacing devices 240, 340 may be formed out of a durable polymer or metallic material such as a blow moulded or injection moulded polymer. The frame 258, 358 surrounds and is formed integrally with the interface surface 260, 360. The interface surface 260, 360 is generally in the form of a surface that is recessed within the frame 258, 358 to form the recess 265, 365 or cavity having a shape that corresponds to, or conforms with, the shape of the external surface of the power tool module 270 or the power control module 370 or at least a portion of the external surfaces of the power tool module 270 or the power control module 370 to be positioned there within.

For example, in the embodiment illustrated in FIGS. 23 to 25, the interface surface 260 is shaped to conform to the external surface of a handheld power drill-type power tool 270. Accordingly, the interface surface 260 illustrated in FIGS. 23 to 25 includes a power drill body housing region 262 shaped to receive a body housing 272 of the power tool and a driven member region 266 shaped to receive the driven member or chuck portion 276 of the power tool 270. As will be appreciated, the interface surface 260 can be designed for any one of a variety of power tools, and modules thereof, of types other than hand held power drills such as jigsaws, angle grinders, polishers, sanders and drivers.

As such, the interface surface 260 may have any one or more of these regions or may have other regions entirely that are adapted to conform with the external surface of the particular power tool to be received within the recess 265 defined by the interface surface 260. The interface surface 260 meets the frame 258 along a peripheral edge 261 extending around the periphery of the interface surface 260 and defining an opening 263 through which the power tool is received to the recess 265.

Figure 26:
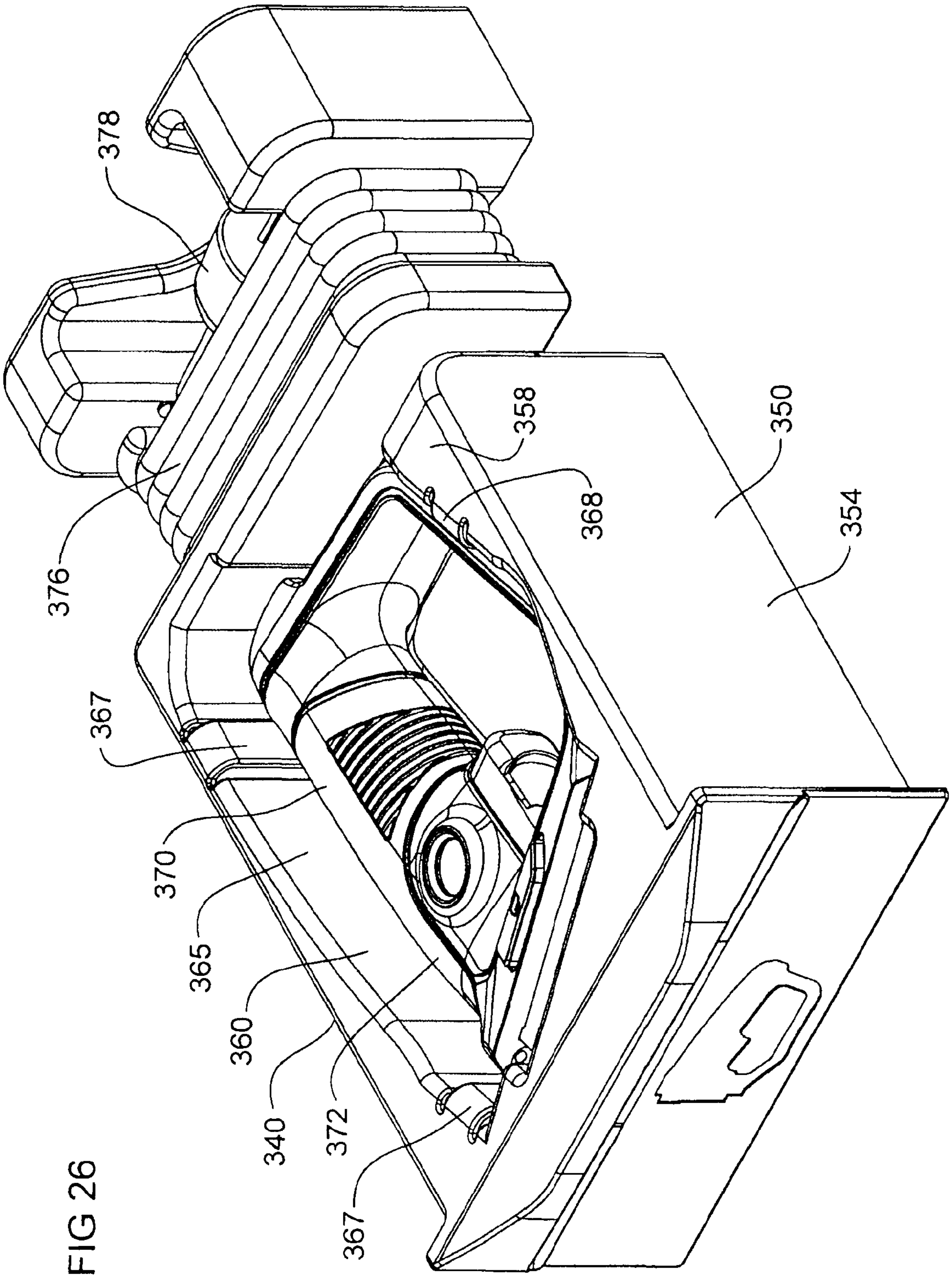
FIG. 26 illustrates a perspective view of an interfacing device of an embodiment of the storage system of the invention wherein the interfacing device contains a power control module capable of attachment to the tool module of FIG. 23.
Figure 27:
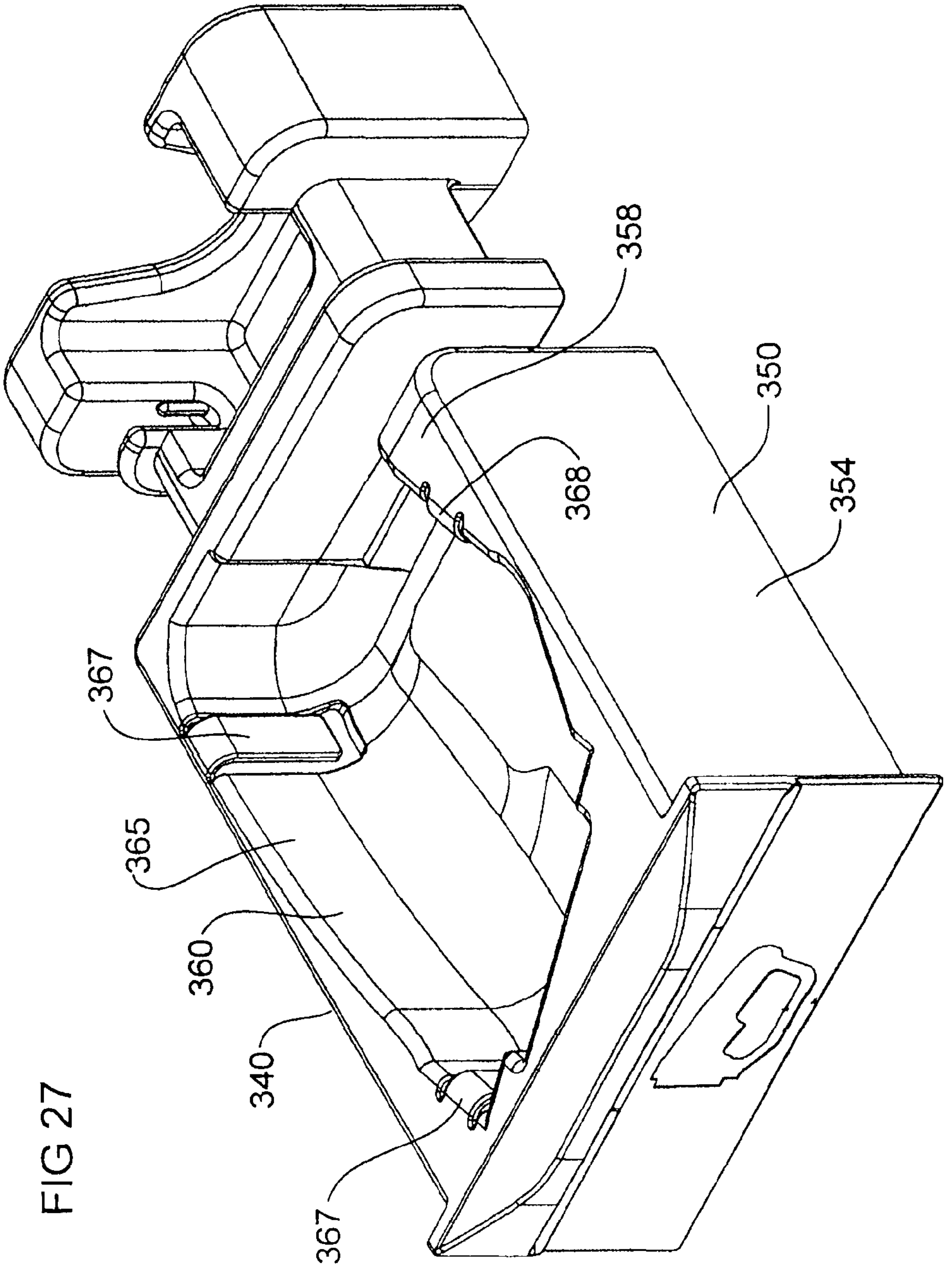
FIG. 27 illustrates a perspective view of the interfacing device of FIG. 26 with the power control module removed.
Figure 28:
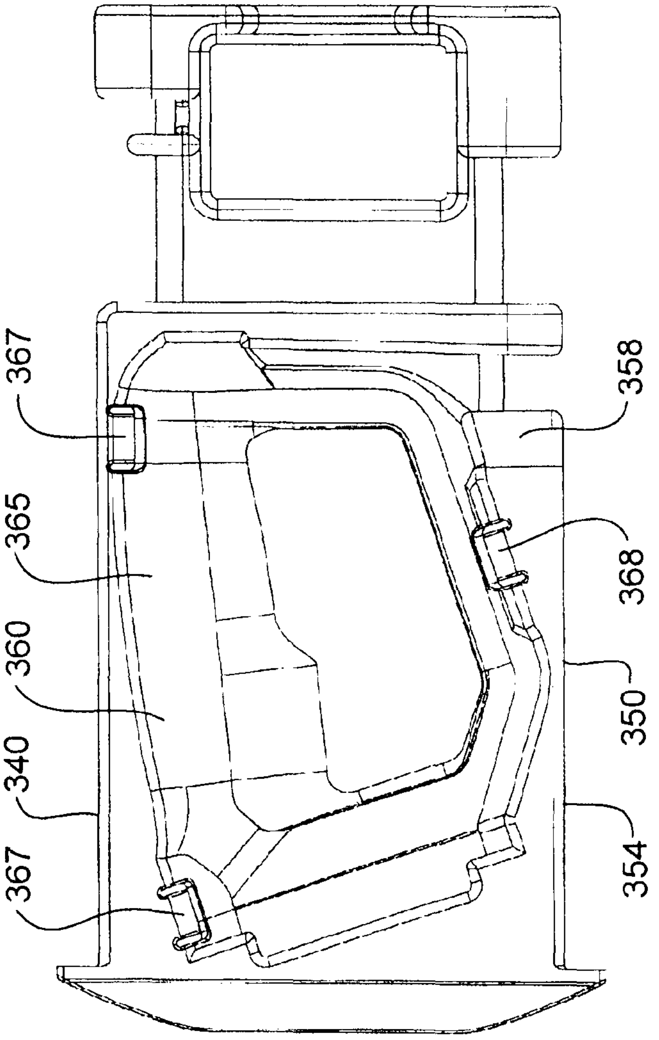
FIG. 28 illustrates a plan view of the interfacing device of FIG. 26 with the power control module removed.

In the embodiment illustrated in FIGS. 26 to 28, the interface surface 360 is shaped to conform to the external surface of a handheld power control module 370. Accordingly, the interface surface 360 illustrated in FIGS. 26 to 28 includes a power control body housing region 362 shaped to receive a body housing 372 of the power control module 370 and a power cord housing region 366 shaped to receive the power cord 376 and connector 378 of the power control module 370. As will be appreciated, the interface surface 360 can be designed for any one of a variety of power control modules 370 or other devices. As such, the interface surface 360 may have any one or more of these regions or may have other regions entirely that are adapted to conform with the external surface of the particular module or device to be received within the recess 365 defined by the interface surface 360. The interface surface 360 meets the frame 358 along a peripheral edge 361 extending around the periphery of the interface surface 360 and defining an opening 363 through which the power control module 370 is received to the recess 365.

The interface surface 260, 360 may be shaped and/or sized so as to receive the power tool module 270 or the power control module 370 in an interference fit there within. In the embodiments illustrated in FIGS. 23 to 28, the interface surface 260, 360 includes one or more pairs of opposing tabs or fingers 267, 268, 367, 368 that are adapted to receive and squeeze the power tool module 270 or the power control module 370 therebetween when the power tool module 270 or the power control module 370 is received within the recess 265, 365 so as to prevent, limit or restrict movement of the power tool module 270 or the power control module 370 relative to the recess 265, 365 and to prevent, restrict or limit removal of the power tool from within the recess 265, 365.

As will be appreciated, the receptacle 10 of embodiments of the invention is capable of receiving any one of a variety of interfacing devices 40, 140, 240, 340 for receiving any one of a variety of devices, such as power tools, therewithin in a manner in which the devices are held securely within and/or relative to the receptacle 10.

Figure 8:
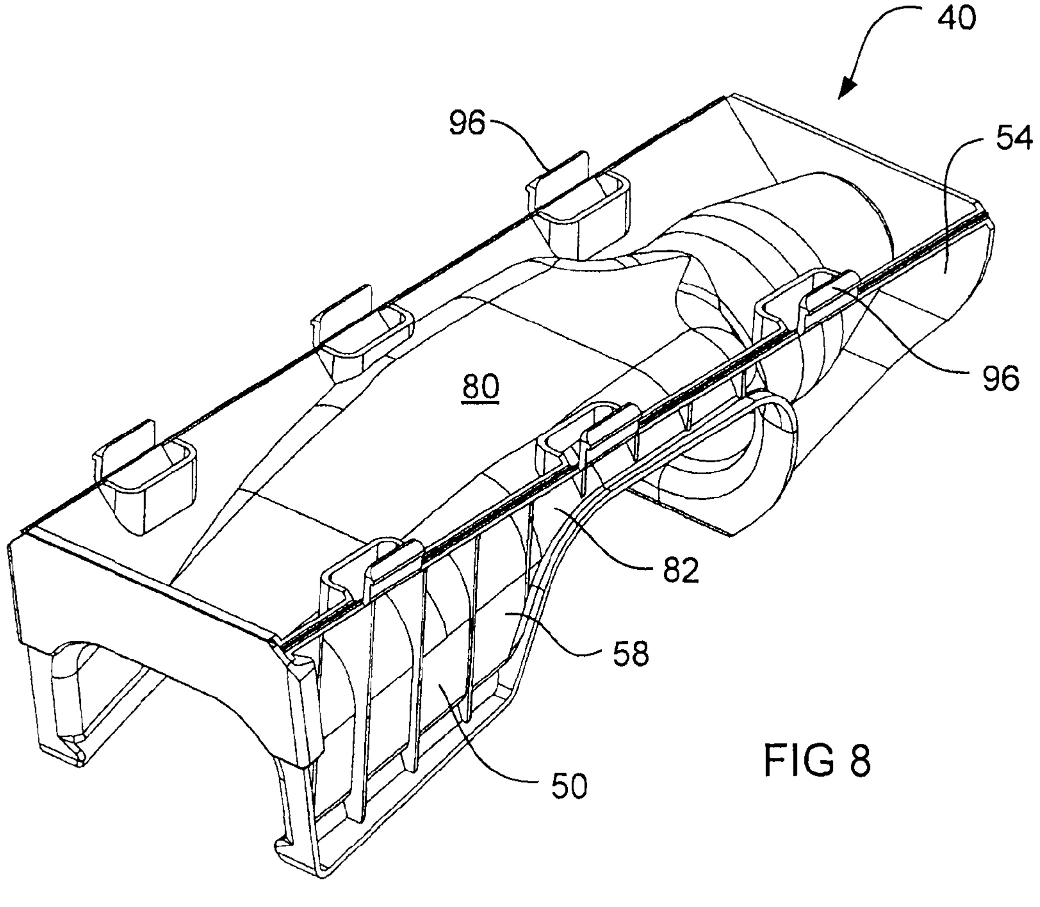
FIG. 8 illustrates a reverse perspective view of the embodiment of the power tool interfacing device of FIG. 7 wherein the interfacing device is in the assembled condition.
Figure 9:
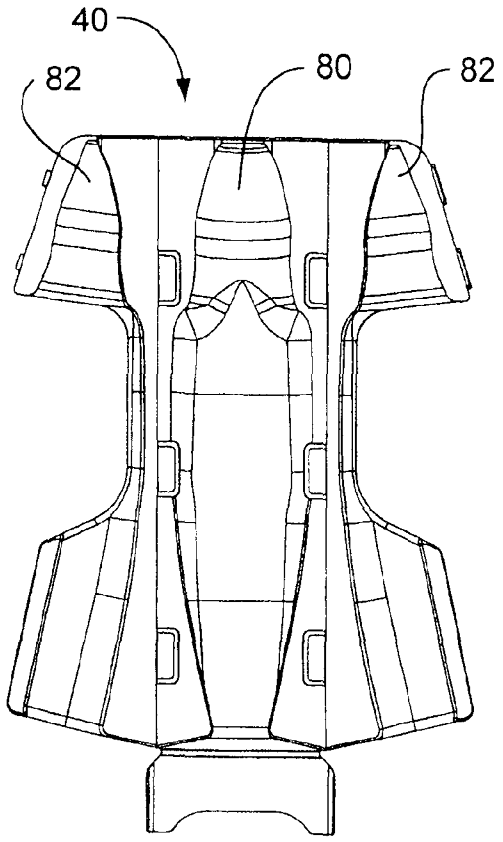
FIGS. 9 to 11 illustrate a top view, a bottom view and an end view of the power tool interfacing device of FIG. 7 wherein the interfacing device is in a lay-flat condition.
Figure 10:
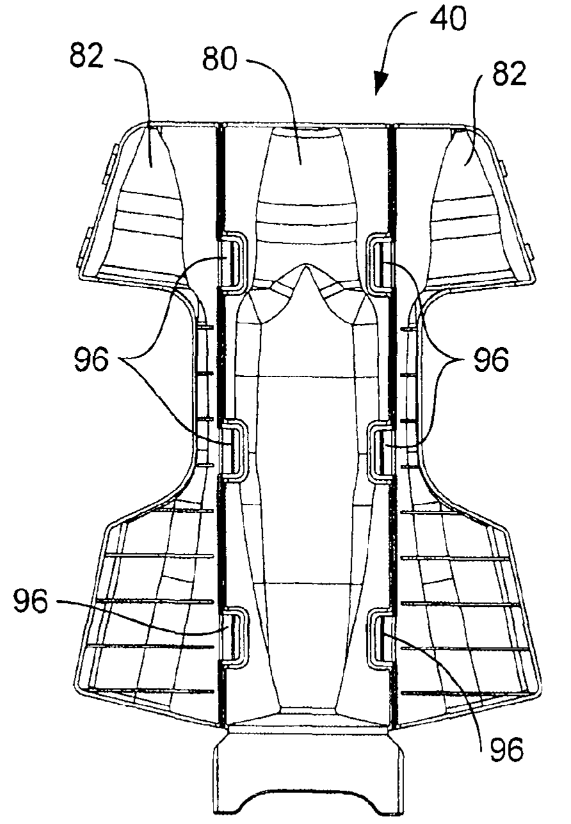
Figure 11:
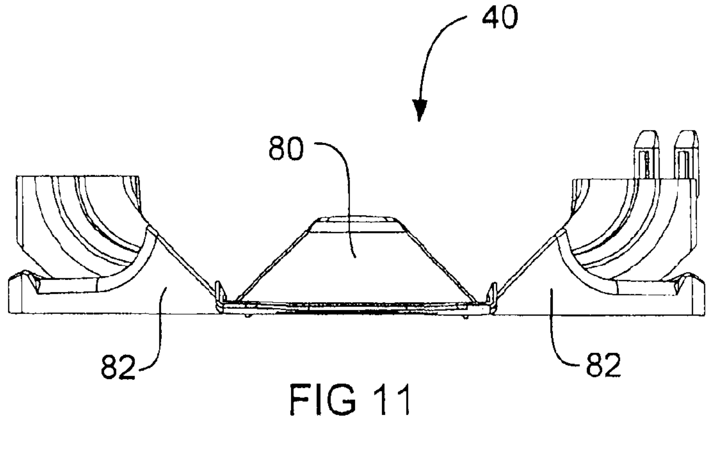
Figure 12:
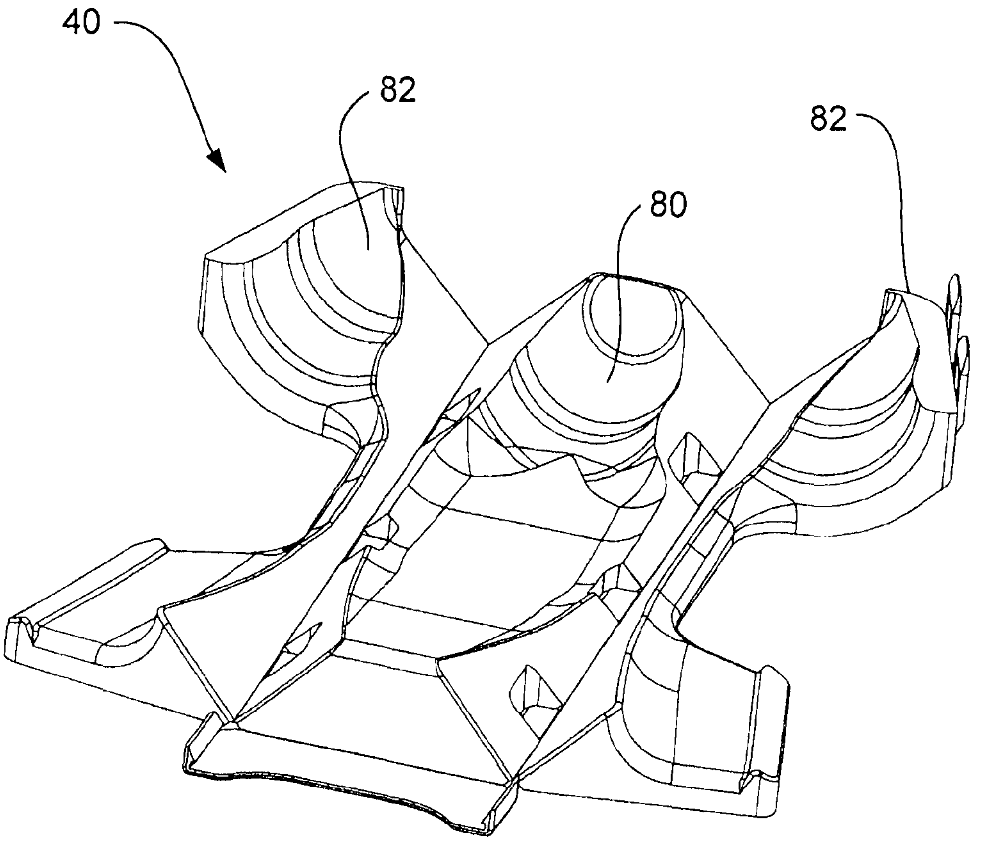
FIG. 12 illustrates a perspective view of the power tool interfacing device of FIG. 7 wherein the interfacing device is in the lay-flat condition.
Figure 13:
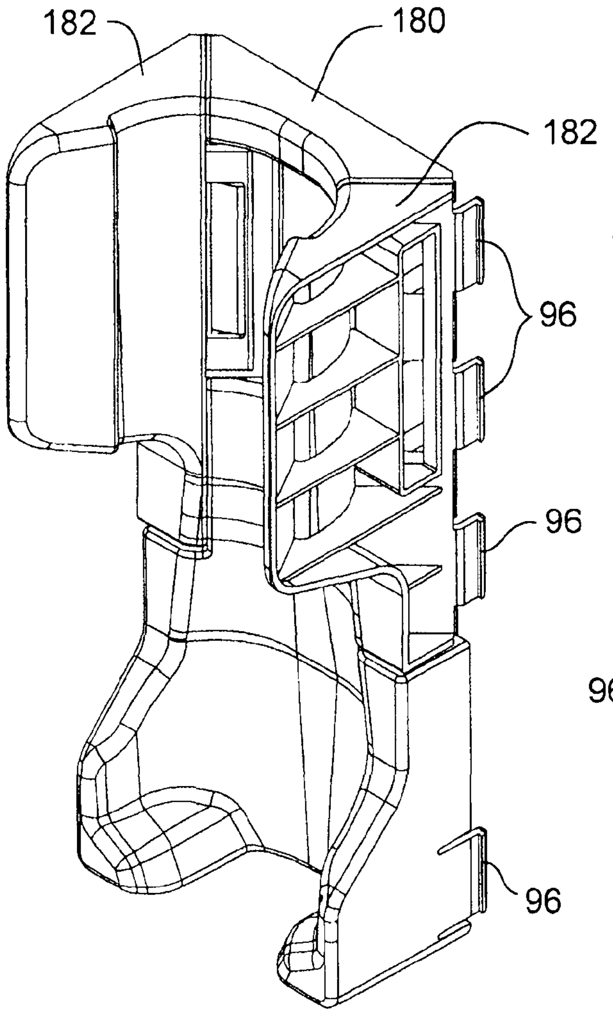
FIG. 13 illustrates a perspective view of a power tool interfacing device of another embodiment of the power tool storage system wherein the interfacing device is in an assembled condition.
Figure 14:
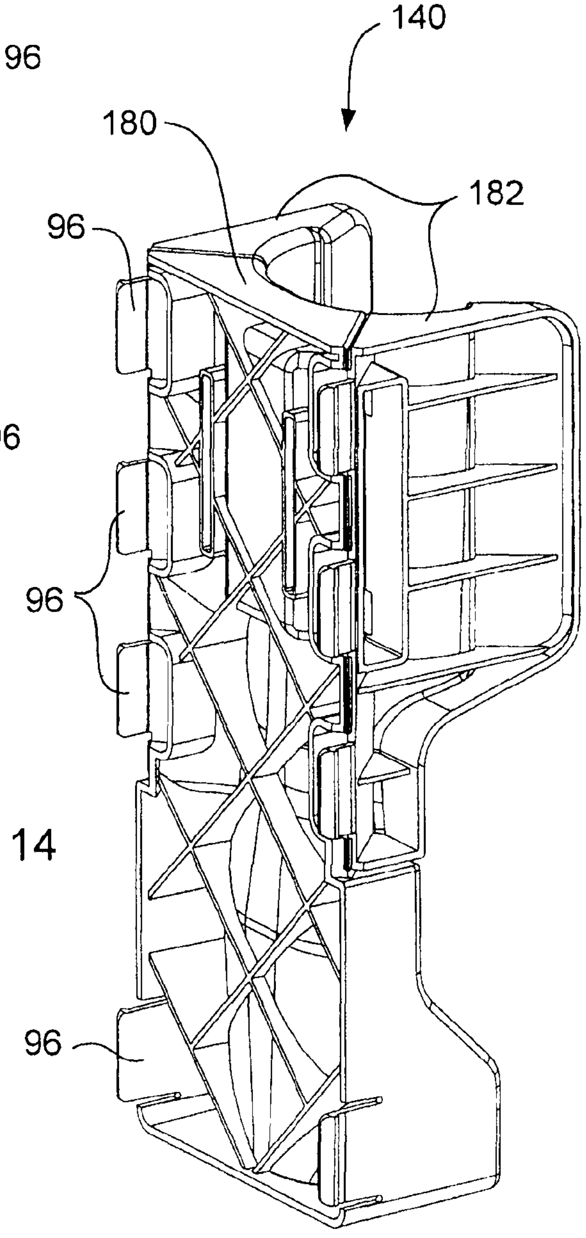
FIG. 14 illustrates a reverse perspective view of the power tool interfacing device of FIG. 13 wherein the interfacing device is in the assembled condition.
Figure 15:
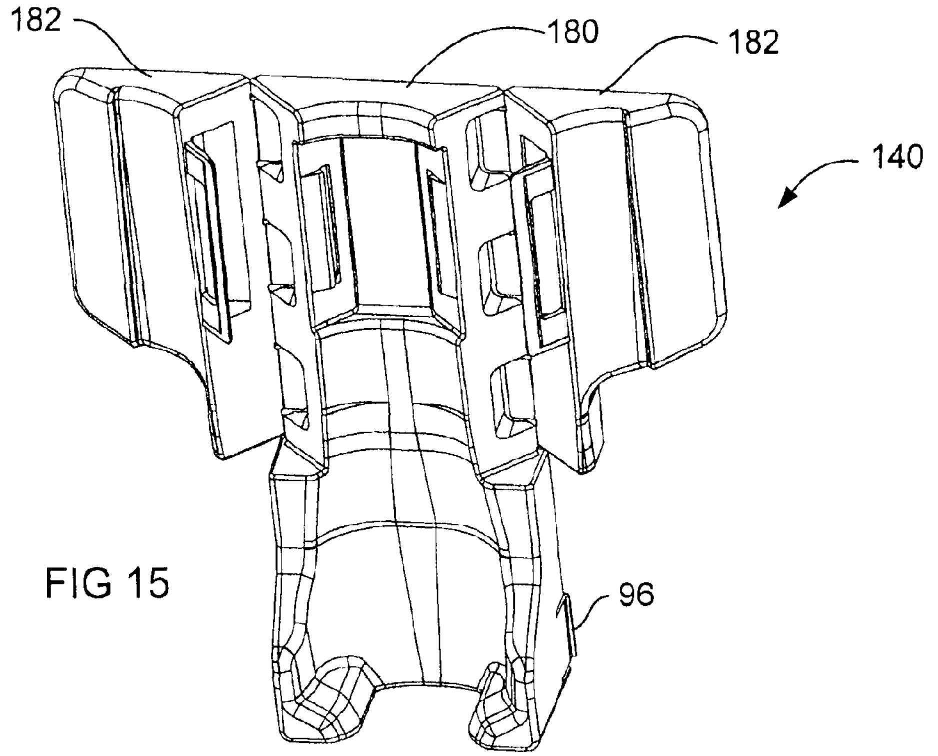
FIG. 15 illustrates a perspective view of a power tool interfacing device of FIG. 13 wherein the interfacing device is in a lay-flat condition.
Figure 16:
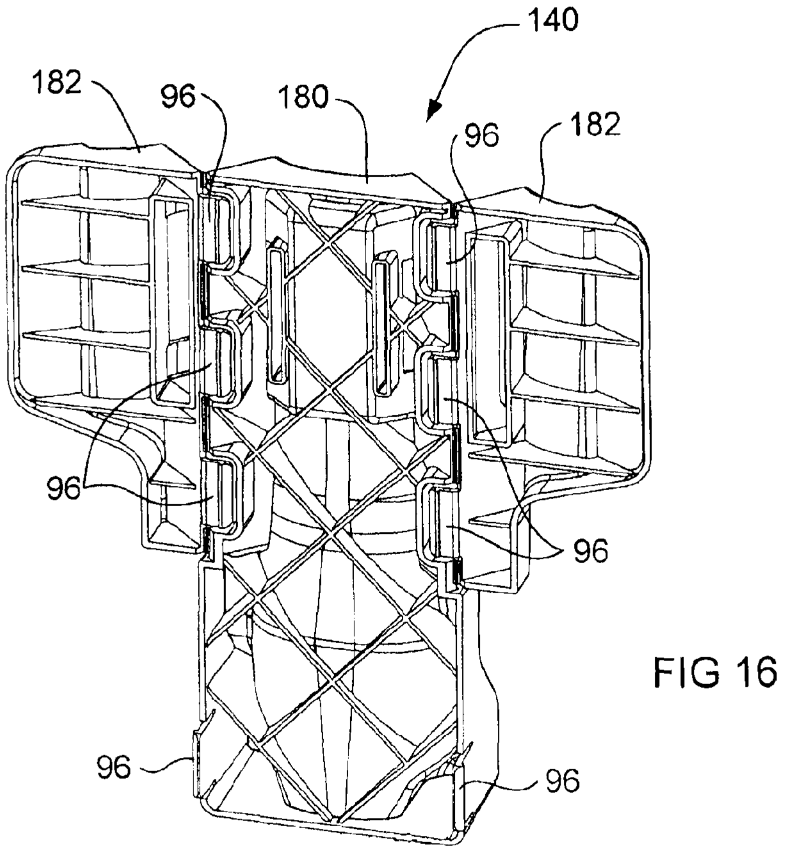
FIG. 16 illustrates a reverse perspective view of the power tool interfacing device of FIG. 13 wherein the interfacing device is in the lay-flat condition.

The storage system 1 of embodiments of the invention includes a connection means for releasably connecting the base 20 of the receptacle 10 with at least one component, such as the interfacing device 40, 140, 240, 340 of embodiments of the invention, such that the component is positioned within the internal space 15 of the receptacle 10. The connection means includes a first connection portion 90 associated with the base 20 for connecting with a second connection portion 95 of the component, such as the interfacing device 40, 140, 240. In the embodiment illustrated in FIGS. 1 to 6, the connection means includes a row of spaced apart pairs of the first connection portions 90, each of the pairs of first connecting portions 90 for connecting with a pair of the second connecting portions 95 of the component, namely the interfacing device 40, 140. Each of the pairs of first connecting portions are comprised of a pair of spaced apart openings 91 for receiving the pair of the second connecting portions 95 comprised of a pair of spaced apart cantilever beam snap-fitting members 96 as best illustrated in FIG. 8. Each one of the cantilever beam members 96 of the second connecting portion 95 are adapted to be received within one of the openings 91 of the first connecting portion 90 in the base wall 22 of the base 20 of the receptacle 10. Thus, when the cantilever beam members 96 of the second connecting portion 95 are adapted to be received within one of the openings 91 of the first connecting portion 90. The interfacing device 40, 140 is thereby releasably connected to the base wall 22 of the base 20 the interfacing device 40 within the internal space 15 thereof. The interfacing device 40, 140 is connected to the base 20 within the internal space 15 thereof in an orientation such that the opening 63 to the recess 65 is presented in a direction towards the opening 19 to the internal space 15 so as to enable a user to insert the power tool through the opening 19 into the internal space 15 and into the recess 65. Once the power tool is inserted into the recess 65 of the interfacing device 40, 140 the power tool can be maintained within the recess 65 by the opposing tabs or fingers 67, 68, that are adapted to receive and squeeze the power tool therebetween when the power tool is received within the recess 65 so as to prevent, limit or restrict movement of the power tool relative to the recess 65 and the receptacle 10. The interfacing device 40, 140 thus prevents, restrict or limit removal of the power tool from within the recess 65 and the internal space 15 within the receptacle 10 unless required by a user.

Figure 2:
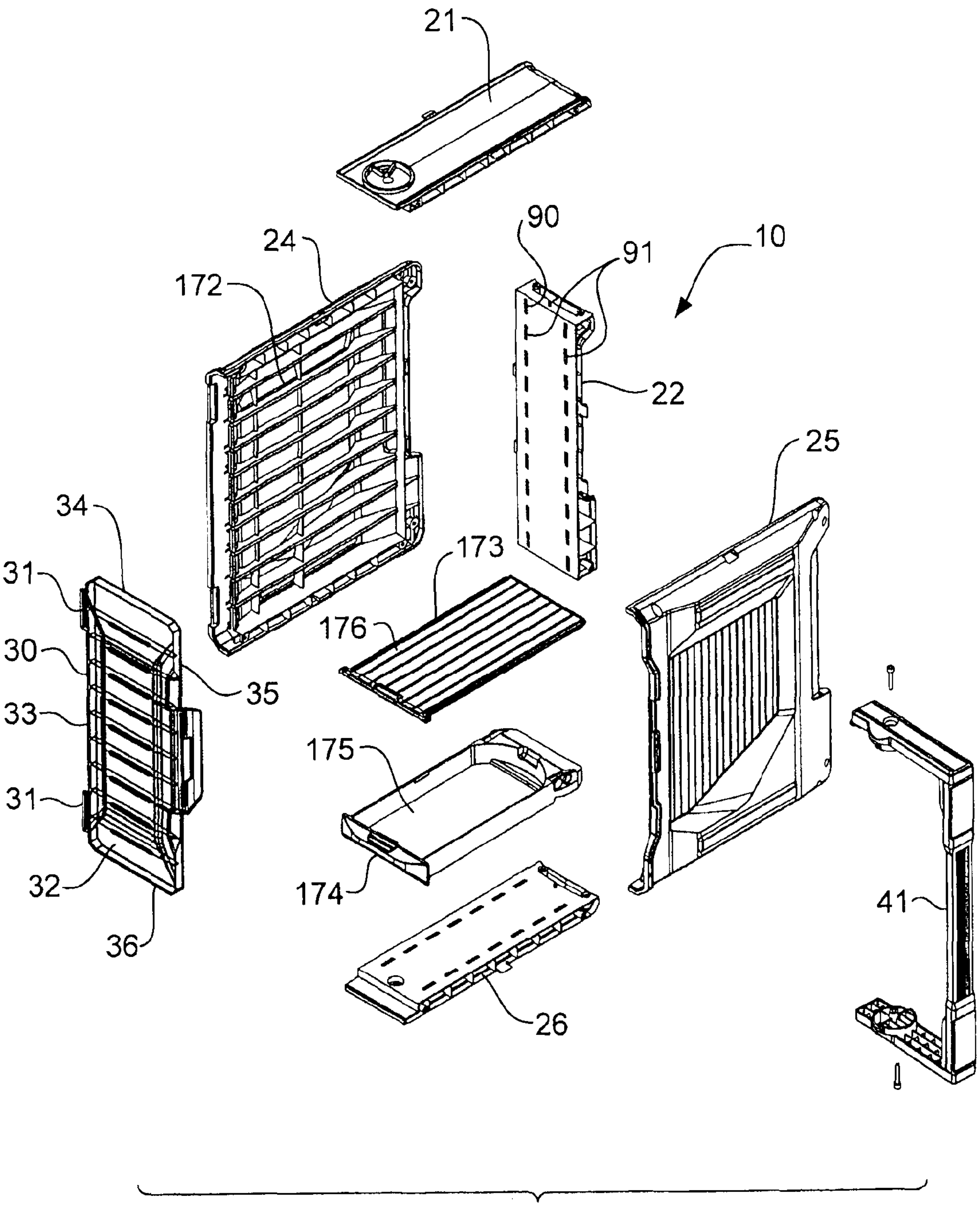
FIG. 2 illustrates an exploded view of the power tool receptacle of FIG. 1.
Figure 7:
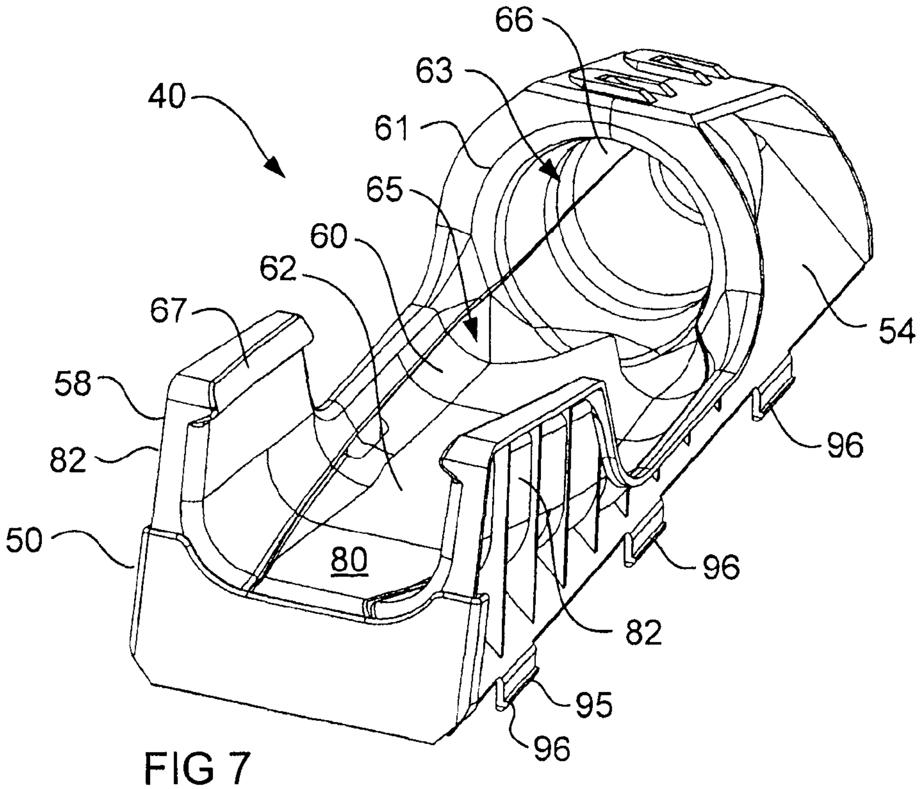
FIG. 7 illustrates a perspective view of a power tool interfacing device of an embodiment of the power tool storage system wherein the interfacing device is in an assembled condition.

As illustrated in FIGS. 7 to 16, the embodiments of the product interfacing device 40, 140 include first folding members 80, 180 and second folding members 82, 182 that are interconnected so as to be foldable relative to each other between a lay-flat condition, such as is shown in FIGS. 9 to 12, 15 and 16 and an assembled condition, such as is shown in FIGS. 7, 8, 13 and 14, wherein in the assembled condition the first folding members 80, 180 and the second folding members 82, 182 are positioned relative to each other so as to form the interface surface 60, 160. Furthermore, in the assembled condition the first folding members 80, 180 and the second folding members 82, 182 are positioned relative to each other so as to form, or reveal, the second connection portion 95 of the product interfacing device 40, 140. In other words, when the first folding members 80, 180 and the second folding members 82, 182 are folded into the assembled condition the second connection portion 95, namely the cantilever beam snap-fitting members 96 of the product interfacing device 40, 140 are made prominent in order to be insertable within the openings 91 of the first connecting portion 90. Thus, the interfacing device 40, 140 can be releasably connected to the base wall 22 of the base 20 the interfacing device 40 within the internal space 15 thereof As illustrated in FIG. 2, the receptacle 10 includes one or more pairs of opposite parallel slots 172 extending from the base wall 22 to the opening 19 that are adapted to receive a respective one of a pair of opposing and parallel flanges, or ridges 173 arranged on a component for the purpose of maintaining the component in a fixed position within the internal space 15 of the receptacle 10. In the embodiment illustrated in FIG. 2, the component that includes the ridges 173 that fit within the slots 172 is a drawer assembly including a drawer 174 that includes a recess 175 and a lid 176. The recess 175 of the drawer is adapted to receive a product such as tool bits, screws or the like. The lid 176 is fixed relative to the base 20 whereas the drawer 174 is movable relative to the base 20 between a closed position for enclosing the recess 175 beneath the lid 176 and an open position for enabling access to the recess 175. Attachment of the component, such as the drawer assembly, to the power tool receptacle 10 involves aligning the parallel slots 172 and the parallel flanges 173 and then sliding the component into the internal space 15 of the receptacle 10 until the component abuts against an internal surface of the base wall 22 of the receptacle 10. The component may then be fixed in position within the receptacle by any suitable means. As shown in FIG. 2, in a preferred embodiment the receptacle 10 includes a plurality of pairs of opposite parallel slots 172 extending from the base wall 22 to the opening 19. Each of the pairs of parallel slots 172 can receive a respective one of a pair of opposing and parallel flanges, or ridges 173 arranged on each of a number of components for the purpose of maintaining each of the components in a fixed position within the internal space 15 of the receptacle 10. For example, a plurality of components, such as a plurality of drawer assemblies each including the drawer 174 and the lid 176 can be received and maintained within the receptacle 10 in a stacked or chest of drawers arrangement.

In the embodiment illustrated in FIGS. 22 to 25, the connection means includes the first connecting portion 90 in the form of the spaced apart pairs of the parallel slots 172, each of the pairs of slots 172 for slidably receiving the pair of the flanges or ridges 273 on the side walls 251, 252 of the product interfacing device 240. Thus, the pair of the flanges or ridges 273 on the side walls 251, 252 of the product interfacing device 240 comprise the second connecting portion 95 of the product interfacing device 240. When the flanges or ridges 273 product interfacing device 240 are aligned with the parallel slots 172 of the receptacle 10 the product interfacing device 240 can be slid into the internal space 15 thereof. As a result, the interfacing device 240 is thereby releasably connected to the base 20 of the receptacle 10 within the internal space 15 thereof. Accessing the power tool module 240 or other device within the recess 265 of the interfacing device 240 involves opening the closure member 30, gripping a handle 253 on a front wall 255 of the interfacing device 240 and sliding the interfacing device 240 at least partially out of the internal space 15 of the receptacle 10. When it is desired to return the power tool module 240 or other device to the recess 265 of the interfacing device 240 a user carries out the same process. Once the power tool module 240 is inserted into the recess 265 of the interfacing device 240 the power tool module 240 can be maintained within the recess 265 by the opposing tabs or fingers 267, 268, that are adapted to receive and squeeze the power tool module 270 therebetween so as to prevent, limit or restrict movement of the power tool module 270 relative to the recess 265 and the receptacle 10. The interfacing device 240 thus prevents, restricts or limits removal of the power tool module 270 from within the recess 265 and the internal space 15 within the receptacle 10 unless and until required by a user.

Figure 22:
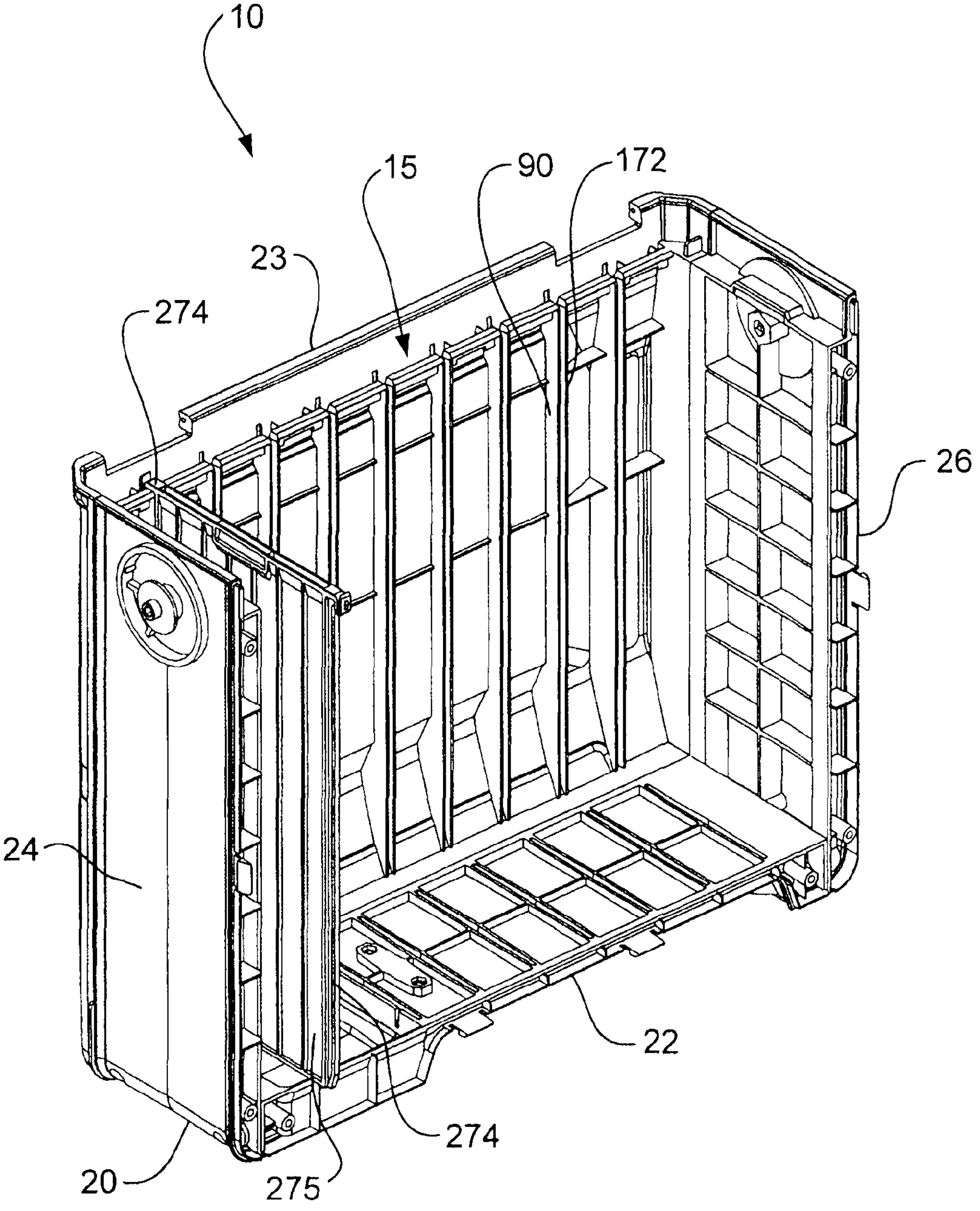
FIG. 22 illustrates a perspective view of another embodiment of the device receptacle of an embodiment of the device storage system of the invention with some components removed to reveal internal components thereof.

As illustrated in FIG. 22, the parallel slots 172 can also slidably receive a respective one of a pair of opposing and parallel flanges, or ridges 274 arranged on lateral edges of a component such as a divider or tray 275 or another component such as a drawer or accessory or hand tool storage tray.

Figure 29:
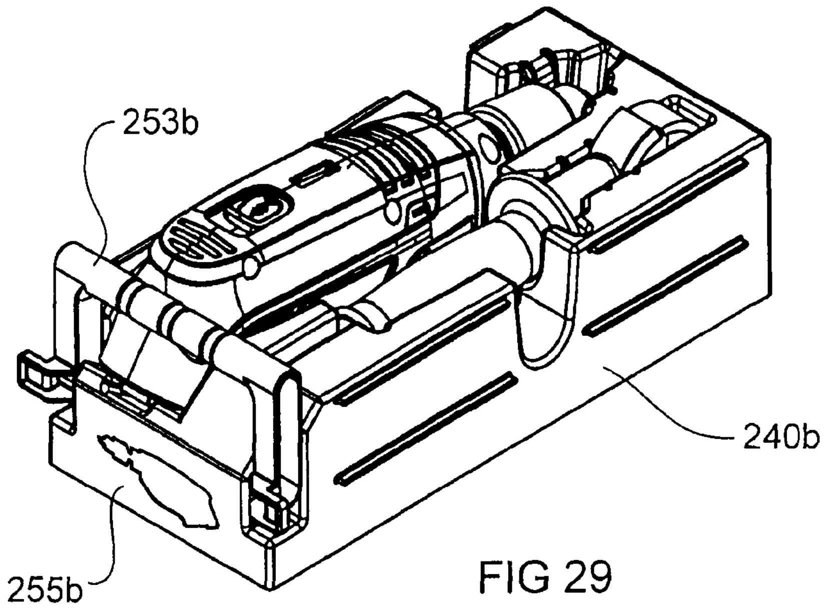
FIG. 29 illustrates a perspective view of a power tool interfacing device of an embodiment of the storage system of the invention wherein the interfacing device contains a hand held power drill module capable of attachment to a power control module and a pivoting handle connected to the interfacing device, the handle in a retracted position.
Figure 30:
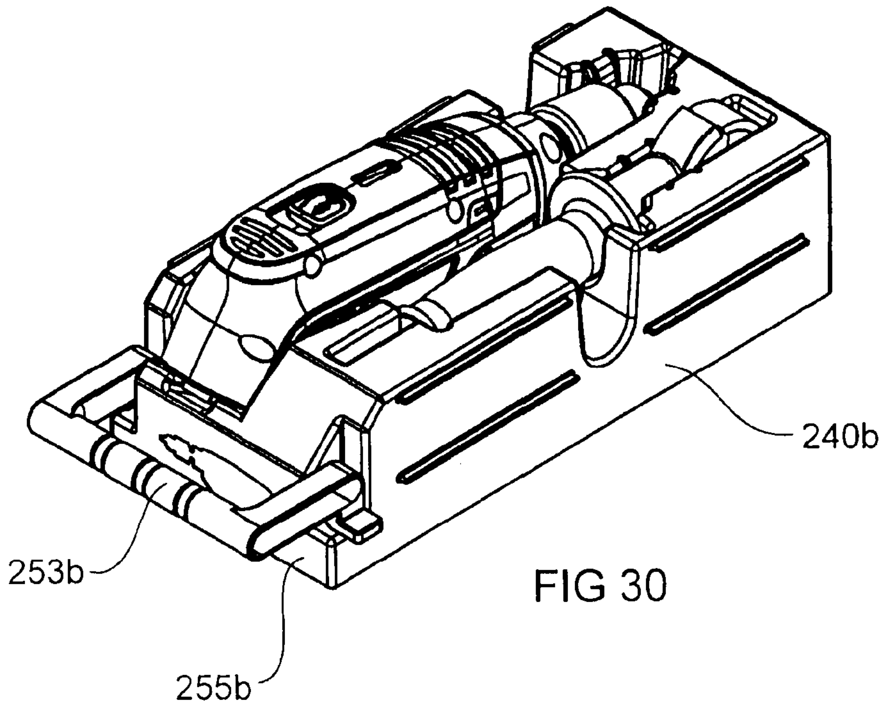
FIG. 30 illustrates a perspective view of the power tool interfacing device of FIG. 29 with the handle in an extended position.

FIGS. 29 and 30 illustrate another embodiment of an interfacing device **240*b* in accordance with the invention in which the interfacing device 240*b* includes a pivoting handle 253*b* on the front wall 255*b* of the interfacing device 240*b*. A user can grip the handle 253*b* and pivot the handle 253*b* from the retracted position shown in FIG. 29 to the extended position shown in FIG. 30 and slide the interfacing device 240*b* at least partially out of the internal space 15 of the receptacle 10. The various embodiments of the interfacing device also include flanges on lateral sides to engage a front edge of the walls of the receptacle to prevent sliding of the interfacing device into the internal space 15** beyond a desired point so as to prevent, for example, the interfacing device from touching the rear internal surface of the receptacle.

In another embodiment (not shown) the interfacing device includes an integrated battery charger device for mounting thereon a power control module including an integrated battery power supply, or a detachable battery power supply, for connection to a power tool. The battery charger incorporated in the interfacing device is operable for charging the battery either separated from the power control module or attached to the power control module when the battery or the power control module are mounted to the interfacing device. The battery charger device includes a power cord that is operable for connecting the battery charger device to a mains power supply.

In embodiments of the invention, the power tool interfacing device 40, 140, 240, 340 may form part of a package for containing the power tool or any other component, such as the modular handle assembly, after manufacture and during subsequent transport and display of the power tool for sale to consumers. The package (not shown) includes the power tool interfacing device 40, 140, 240, 340 and a removable cover (not shown) that is removably coupled to the interfacing device 40, 140, 240, 340 for covering the power tool when the power tool is received within the recess 65, 165, 265, 365 of the power tool interfacing device 40, 140, 240, 340. When the removable cover is coupled to the interfacing device 40, 140, 240, 340 the cover is operable for covering the power tool and preventing removal of the power tool from the interfacing device 40, 140, 240, 340. The removable cover is removable from the interfacing device 40, 140, 240, 340 to enable access to the power tool within the recess 65, 165, 265, 365 and removal of the power tool from within the recess 65, 165, 265, 365. The removable cover may be formed out of any suitable material such as a transparent polymer material that may completely surround the interfacing device 40, 140, 240, 340 and the power tool or may cover the power tool and at least part of the power tool interfacing device 40, 140, 240, 340. The removable cover may alternatively be in the form of a disposable box containing the interfacing device 40, 140, 240, 340 and the power tool there within. The removable cover may be formed out of a transparent polymer material that is thermo-formed to conform to the exterior shape of the power tool contained within the recess 65, 165, 265, 365, or at least a portion of the exterior shape of the power tool projecting from the recess 65, 165, 265, 365. The removable cover may be formed out of transparent material to provide a viewing portion to enable a consumer to view the power tool contained within the package. Forms of the package may include a printed carton containing the interfacing device 40, 140, 240, 340 which forms a strong and resilient holder for a power tool contained within the package. Accordingly, the interfacing device 40, 140, 240, 340 replaces foam or cardboard as a means for holding the power tool within the package and restricting movement of the power tool within the package during shipping and transport.

The package is advantageous in that it provides a package for containing the power tool for marketing and display for sale to consumers that is relatively inexpensive to manufacture compared with a package for a power tool in the form of a durable container or case formed out of a rigid polymer or metallic material. Accordingly, the package provides a relatively inexpensive means for containing the power tool for transport, marketing and display for sale and enables the power tool to be marketed at a lower price than if the power tool were packaged within a durable container or case. The package is also advantageous in that it provides the power tool interfacing device 40, 140, 240, 340 which can be used in conjunction with the receptacle 10 that is separately marketed and sold. The power tool interfacing device 40, 140, 240, 340 that comes with the packaging associated with the power tool can be releasably connected to the receptacle with within the internal space 15 of the receptacle 10 to thereby securely receive and contain the power tool throughout the usable life of the power tool. Thus, the receptacle 10 can be used as a case for carrying the power tool whereby the power tool is held and maintained in a secure and steady position within the internal space 15 of the receptacle 10. Furthermore, because the receptacle 10 includes the first connection portion 90 and the component such as the interfacing device 40, 140, 240, 340 includes the second connection portion 95 the receptacle 10 can receive any one or more of a variety of interface members 40, 140, 240, 340 respectively including a recess 65, 165, 265, 365 shaped to receive any one of a variety of products therewithin such as, for example, a handheld power drill, handheld power saw, handheld power screwdriver, handheld percussion/hammer drill, handheld angle grinder, handheld circular saw, handheld power sander and any other handheld electrical device such as a light emitting device, such as a torch, or a radio to name but a few.

Accordingly, an overall advantage of the power tool storage system 1 and the power tool package of the invention is that it provides a package including the interfacing device 40, 140, 240, 340 that is relatively inexpensive to manufacture and can be used to market products, such as power tools, to consumers at a competitive price provide whilst also providing the consumer with the option of separately purchasing the receptacle 10 and interchangeably placing and connecting any one of a variety of power tool interface members 40, 140, 240, 340 within the internal space 15 of the receptacle 10. Thus, the receptacle 10 is adapted to receive and contain the product, such as a power tool, there within in a secure and stable manner similar to the way in which this is achieved with existing durable power tool storage cases formed out of durable and substantially rigid polymer or metallic materials specifically designed to contain only one power tool throughout the life thereof. The invention is also advantageous in that the receptacle 10 including the interfacing device 40, 140, 240, 340 can be used to transport and carry the receptacle 10 with the power tool there within whilst holding the power tool within the receptacle 10 in a relatively stable position.

In another form, not illustrated, the receptacle 10 can be configured to become the housing of a product, such us a portable audio device or a portable power module containing means to supply power to one or more electrical devices such as hand held power tools.

Figure 17:
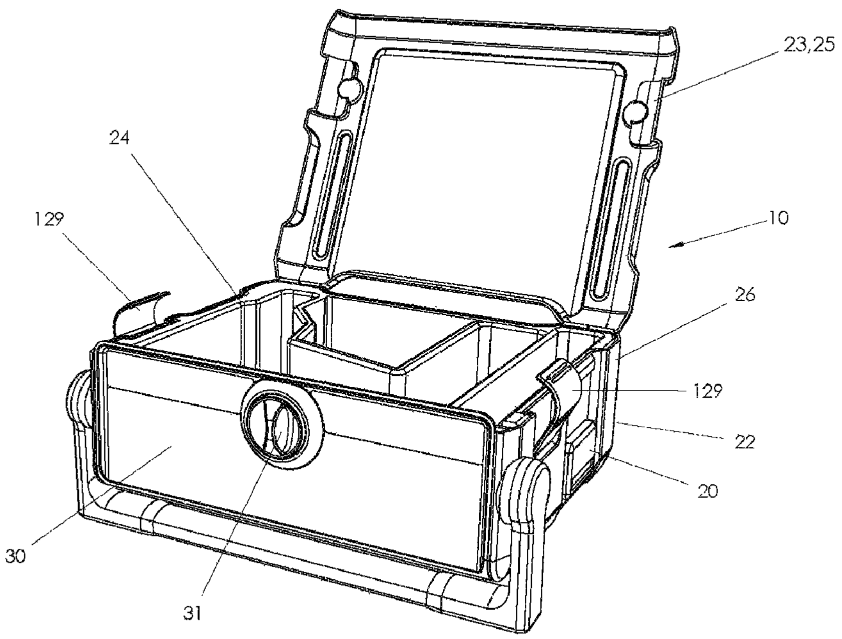
FIG. 17 illustrates a perspective view of another embodiment of the power tool receptacle.
Figure 18:
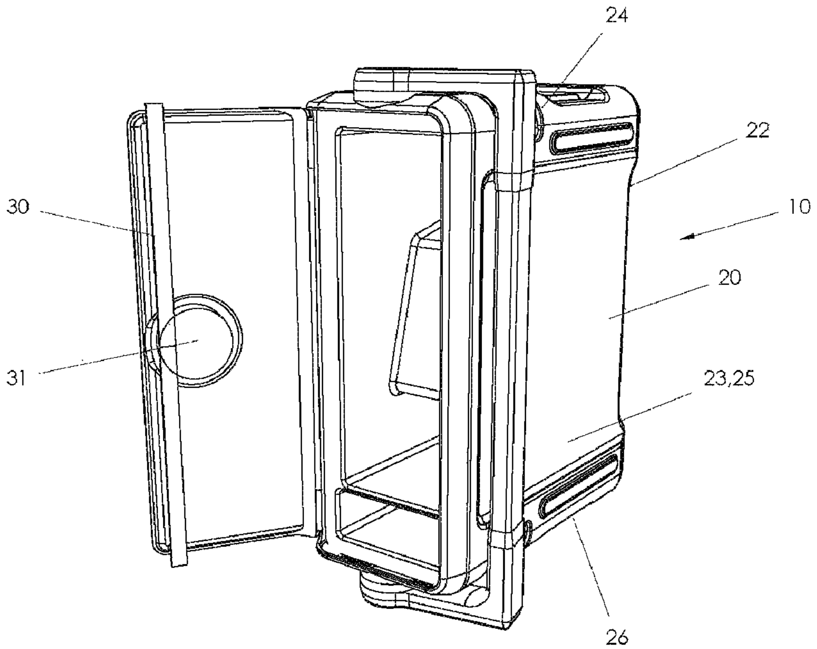
FIG. 18 illustrates another perspective view of the embodiment of the power tool receptacle illustrated in FIG. 17.

Referring to FIGS. 17 and 18, in an embodiment of the receptacle 10 the base 20 can include a base wall member 22, pair of opposite side wall members 23, 25, a pair of opposite end wall members 24, 26 wherein either one or both of the side wall members 23, 25 is pivotally connected to the base wall member 22. Thus, either one of the side wall members 23, 25 can be opened to facilitate access to the internal space 15 within the base 20 of the receptacle 10. The pivotally attached one of the wall members 23, 25 is openable as illustrated in FIG. 17 to facilitate access to the internal space 15 and is closable and lockable in a closed position via one or more latch members 129. As can be seen in FIG. 18, the closure 30 is also pivotally connected to the base 20 to selectively close the opening 19 as in the embodiment illustrated in FIGS. 1 to 6 to selectively allow or prevent access to the internal space 15 within the base 20. The closure 30 also includes a locking mechanism 31 that is operable to selectively lock the closure 30 in the closed position.

Figure 19:
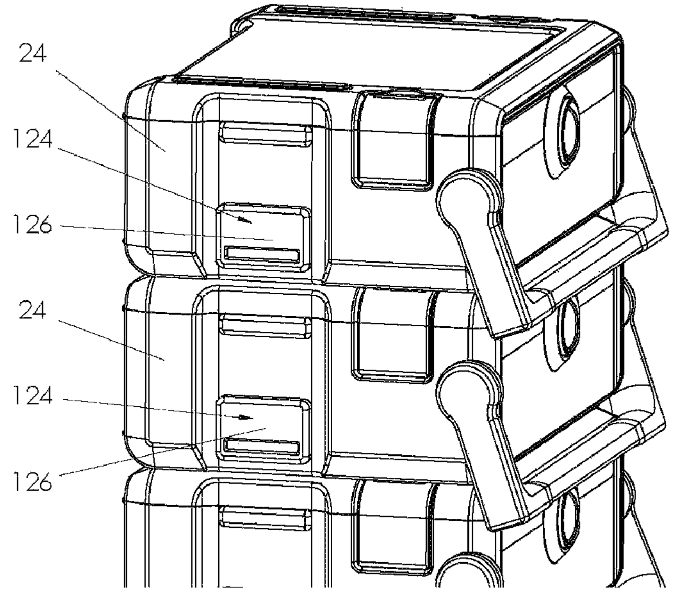
FIG. 19 illustrates a perspective view of a plurality of the power tool receptacles of FIG. 17 stacked upon one another.
Figure 21:
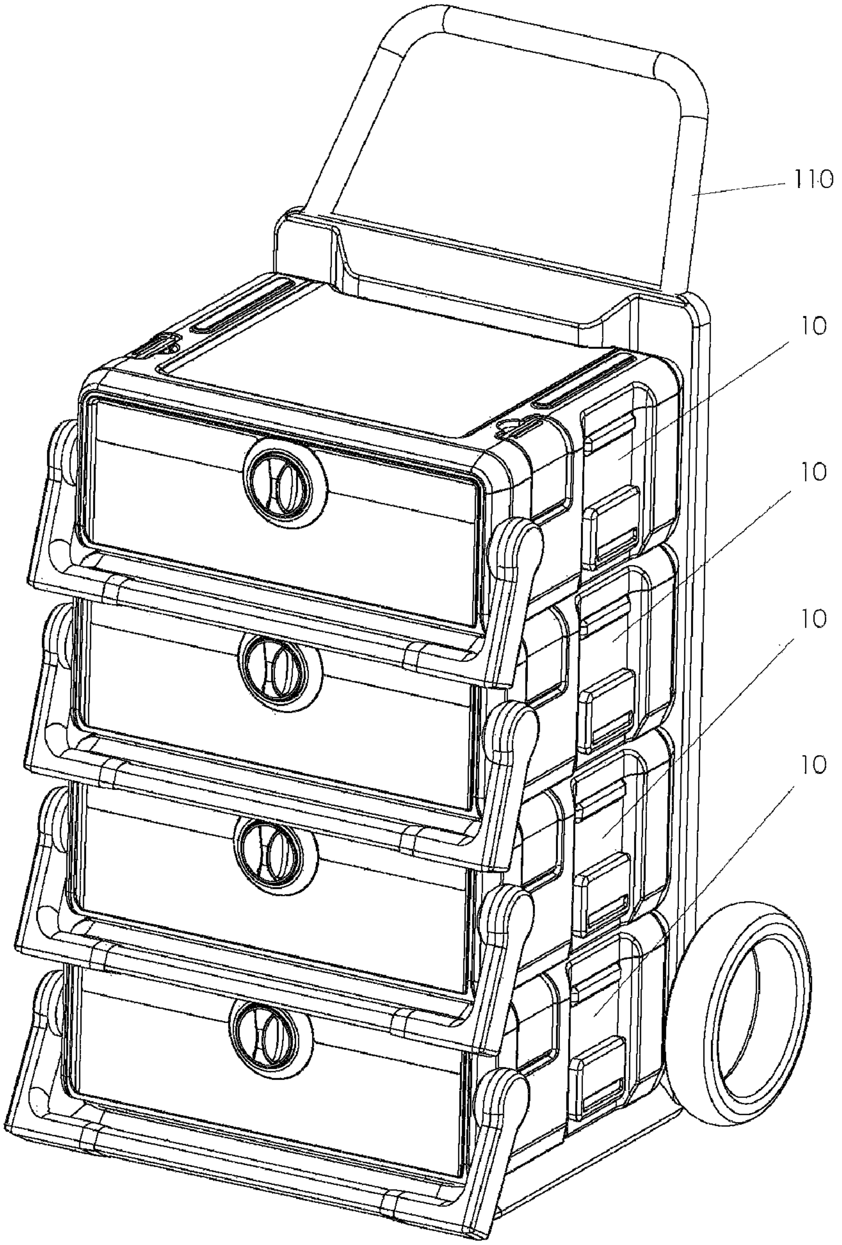
FIG. 21 illustrates a perspective view of plurality of the power tool receptacles of FIG. 17 stacked upon a trolley.

As can be seen in the embodiment illustrated in FIGS. 19 and 21, the receptacle 10 can include a base 20 having interconnecting members 124 that are adapted to interconnect two or more of the receptacles 10 together. Each receptacle can include a base 20 including opposite end wall members 24, 26 that each include an interconnecting member 124 in the form of one or detent members, that may be slidable between an active condition and an inactive condition, wherein in the active condition the interconnecting member 124 is adapted to snap-fit into an interconnecting recess 126 of an adjacent stacked receptacle 10. Each adjacent pair of receptacles 10 is thereby interconnected via a pair of interconnecting members 124 snap-fitting into a pair of interconnecting recesses 126 with one side wall members 23 of one receptacle 10 arranged face to face with another side wall member 25 of another receptacle 10. In yet another form, as illustrated in FIG. 21, one or more of the receptacles 10 may be positioned on a trolley 110. Where more than one of the receptacles 10 is to be stacked on the trolley 110, the receptacles 10 may be interconnected via the interconnecting members 124 snap-fitted into the interconnecting recesses 126. A receptacle 10 may be released from an adjacent receptacle 10 by manually undoing the snap-fit between the interconnecting members 124 and the interconnecting recesses 126 of the adjacent receptacles 10. An advantage of the provision of means to interconnect adjacent and stacked receptacles 10 together is to enable a plurality of the receptacles to be transported either independently or on the trolley 110 with less risk of the stacked receptacles 10 toppling over.

Finally, it is to be appreciated and understood that various alterations, modifications and/or additions may be introduced into the constructions and arrangements of the parts previously described without departing from the spirit or ambit of the invention.

The invention claimed is:

1. A portable storage system including a component for storing a product, comprising:

a receptacle including a base and a closure connected to the base, the base and the closure defining an internal space for receiving one or more components, the closure being operable for selectively enclosing the internal space, at least one component that is positioned within the internal space of the receptacle for accommodating the product, a connection means for releasably connecting the base with the at least one component, the connection means including a first connection portion associated with the base for cooperating with a second connection portion of the component, wherein the first and second connection portions include a ridge and a groove, wherein the groove is configured to receive the ridge so that the at least one component can slide relative to the base to access the product; and wherein the base comprises at least two wall members, the wall members and the closure being connected to each other to define the internal space for receiving the component wherein the closure is operable for selectively enclosing the internal space, at least two of the wall members including the grooves of the first connection portion.

2. The portable storage system of claim 1, wherein the base comprises at least two wall members that define the internal space when in an assembled condition and that are configured to be flat packed in a disassembled condition.

3. The portable storage system of claim 1, wherein the connection means comprises a pair of the ridges arranged on the component.

4. The portable storage system of claim 1, wherein the component is a product interfacing device that includes an interface surface defining a recess that is shaped to conform with an exterior surface of a product and thereby restrict movement of the product relative to the product interfacing device.

5. The portable storage system of claim 4, wherein the product interfacing device includes opposing tabs for receiving and squeezing the product therebetween when the product is received within the recess.

6. The portable storage system of claim 5, wherein the product interfacing device forms part of a package for containing the product independently of the receptacle.

7. The portable storage system of claim 1, wherein the one or more components comprises one or more drawers each drawer including a recess for receiving a product, and wherein each one of the drawers is movable relative to the base between a closed position for enclosing the product within the recess and an open position for enabling access to the product within the recess.

8. The portable storage system of claim 7, wherein the first and second connection portions comprise a ridge and a groove, wherein the groove is configured to slidably receive the ridge to retain the drawer within the internal space of the receptacle.

9. The portable storage system of claim 1, wherein the product is any one of a group consisting of a power tool, an electrical device, an electronic device, a hand held power tool, a hand held electrical device and a hand held electronic device and combinations thereof.

10. A package for containing a product comprising:

a product interfacing device including an interface surface defining a recess that is shaped to conform with an exterior surface of the product and thereby restrict movement of the product relative to the product interfacing device, wherein the product interfacing device includes a connection means for releasably connecting the product interfacing device within an internal space of a receptacle, wherein the connection means includes a first connection portion associated with the product interfacing device for connecting with a second connection portion located within the internal space of the receptacle, wherein the first and second connection portions comprise a ridge and a groove, wherein the groove is configured to slidably receive the ridge to maintain the product interfacing device relative to the receptacle; and wherein the interface surface includes opposing tabs for receiving the product therebetween when the product is received within the recess.

11. The package claim 10, wherein the product interfacing device comprises pivoting handle member for carrying the product interfacing device.

12. A portable storage receptacle for a product, comprising:

a base comprised of a pair of wall members and a closure, the wall members and the closure are connected to each other in an assembled condition to define an internal space for receiving a product wherein the closure is operable for selectively enclosing the internal space, the receptacle being adapted to cooperate with at least one other receptacle to form a modular assembly, at least one component that is positioned within the internal space of the receptacle for accommodating the product, and a connection means for releasably connecting the base with the at least one component, the connection means including a first connection portion associated with the base for cooperating with a second connection portion of the component, wherein the first and second connection portions include a ridge and a groove, and wherein the groove is configured to receive the ridge so that the at least one component can slide relative to the base to access the product.

13. The portable storage receptacle of claim 12, wherein the wall members are configured to be flat packed in a disassembled condition.

14. The portable storage receptacle of claim 12, wherein the wall members are connected together in a clam-shell arrangement in the assembled condition.

15. The package of claim 10, wherein the product interfacing device includes a rotatable handle member that occupies a portion of the internal space within the receptacle and adjacent the product interfacing device.

16. The portable storage receptacle of claim 12 wherein the receptacle includes interconnecting members which are adapted to releasably couple with the other storage receptacle when the storage receptacles are stacked.

17. The portable storage receptacle of claim 12 which is further adapted for removable attachment to a trolley.

18. The package of claim 10 including a cover removably coupled to the interfacing device, wherein the cover is transparent.

* * * * *